(12) United States Patent
Schmitz

(10) Patent No.: US 12,127,805 B1
(45) Date of Patent: *Oct. 29, 2024

(54) HIGHLY MANEUVERABLE SURGICAL CATHETER AND DRIVE SYSTEM

(71) Applicant: Gregory P. Schmitz, Los Gatos, CA (US)

(72) Inventor: Gregory P. Schmitz, Los Gatos, CA (US)

(73) Assignee: Syncrobotix, Inc., Los Gatos, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/634,962

(22) Filed: Apr. 14, 2024

Related U.S. Application Data

(63) Continuation-in-part of application No. 18/593,893, filed on Mar. 2, 2024, which is a continuation-in-part
(Continued)

(51) Int. Cl.
*A61B 1/00* (2006.01)
*A61B 1/005* (2006.01)
(Continued)

(52) U.S. Cl.
CPC .......... *A61B 34/30* (2016.02); *A61B 1/00149* (2013.01); *A61B 1/0055* (2013.01); *A61B 1/018* (2013.01); *A61B 1/2676* (2013.01); *A61B 2034/301* (2016.02); *A61B 2034/303* (2016.02); *A61M 25/0113* (2013.01); *A61M 25/0138* (2013.01)

(58) Field of Classification Search
CPC ..... A61B 34/30; A61B 34/71; A61B 18/1492; A61B 2034/301; A61B 2034/303; A61B 2034/715; A61B 1/0057; A61B 1/01; A61B 1/0051; A61B 1/00071; A61B 1/0149; A61B 1/0055; A61B 1/0125; A61B 1/018; A61B 1/05; A61B 1/2676; A61B 1/0052; A61B 2090/3966; A61B 2017/00331; A61B 2017/00323; A61M 25/0138
USPC ................................................. 600/130, 114
See application file for complete search history.

(56) References Cited

U.S. PATENT DOCUMENTS 11,033,342 B2   6/2021  Schmitz
2006/0069310 A1*  3/2006  Couvillon, Jr. ........ A61B 1/009
                                                              600/152
(Continued)

*Primary Examiner* — Timothy J Neal
*Assistant Examiner* — James Edward Boice
(74) *Attorney, Agent, or Firm* — Stephen E. Zweig

(57) ABSTRACT

Catheter device and driving system configured to navigate the catheter through complex narrow tissue openings such as lung bronchi pathway openings of 3 millimeters or less. The device comprises a proximal catheter portion containing a hollow torque shaft, with a distal catheter portion connected to the proximal portion connected to this torque shaft. The distal position of the catheter is controlled by at least one steering cable/tensioning cable arrangement. The system uses processor-controlled actuators that simultaneously rotate the torque shaft and the at least one steering cable/tensioning cable in a 1:1 relationship, while also actuating the steering cable. The catheter is tipped by a tool plate, which can be equipped with various sensors and other instruments and connected to the outside via other conduits.

21 Claims, 32 Drawing Sheets

Related U.S. Application Data of application No. 18/422,454, filed on Jan. 25, 2024, which is a continuation-in-part of application No. 18/324,493, filed on May 26, 2023, now Pat. No. 11,950,765.

(60) Provisional application No. 63/618,832, filed on Jan. 8, 2024, provisional application No. 63/603,757, filed on Nov. 29, 2023, provisional application No. 63/499,218, filed on Apr. 29, 2023.

(51) Int. Cl.
  *A61B 1/018*   (2006.01)
  *A61B 1/267*   (2006.01)
  *A61B 34/30*   (2016.01)
  *A61M 25/01*   (2006.01)

(56) References Cited

U.S. PATENT DOCUMENTS

| | | |
|---|---|---|
| 2019/0246873 A1* | 8/2019 | Lu .................. A61B 1/0623 |
| 2021/0068619 A1* | 3/2021 | Shin ................. A61B 1/0055 |
| 2021/0100627 A1 | 4/2021 | Soper et al. |
| 2021/0137620 A1 | 5/2021 | Wallace et al. |
| 2022/0087755 A1 | 3/2022 | Romo et al. |
| 2022/0304550 A1 | 9/2022 | Romo et al. |
| 2022/0313375 A1 | 10/2022 | Zhang et al. |

\* cited by examiner

HIGHLY MANEUVERABLE SURGICAL CATHETER AND DRIVE SYSTEM

CROSS-REFERENCE TO RELATED APPLICATIONS

This application is a continuation in part of U.S. patent application Ser. No. 18/593,893, filed Mar. 2, 2024; application Ser. No. 18/593,893 was a continuation in part of U.S. patent application Ser. No. 18/422,454, filed Jan. 25, 2024; Application Ser. No. 18/422,454 was a continuation in part of U.S. patent application Ser. No. 18/324,493, filed May 26, 2023; Application Ser. No. 18/422,454 also claimed the priority benefit of U.S. provisional application 63/603,757 filed Nov. 29, 2023, and U.S. provisional application 63/618,832, filed Jan. 8, 2024; application Ser. No. 18/324,493 claimed the priority benefit of U.S. provisional application 63/499,218, filed Apr. 29, 2023. The entire contents of all of these applications are incorporated herein by reference.

BACKGROUND OF THE INVENTION

Field of the Invention

This invention is in the field of robotic surgery, as well as robotic systems and methods for operating surgical catheters and bronchoscopes.

Description of the Related Art

Medical and surgical catheters, and more specialized versions of such catheters, such as bronchoscopes, are medical devices commonly used for medical diagnosis and treatment. Such "snake-like" devices are designed to traverse various body lumens, such as arteries, veins, portions of the urinary, gastrointestinal, and reproductive systems, and various portions of the respiratory system and lungs. These devices are frequently used for other surgical applications as well.

Some medical devices are formed from long continuous tubes, often from medical-grade polymers. Other such devices may comprise articulated sections formed from a plurality of smaller components often linked together by flexible joints. Such articulated devices themselves may often then be covered with an optional flexible medical plastic grade polymer as well.

Some of these medical devices are intended for direct manipulation by the surgeon or other healthcare professional. Other such devices may also have various motorized, processor-controlled, and even robotically driven accessories. These are often used for greater precision and control.

Examples of such devices include various US patents and patent applications, such as Wallace, US20210137620 A1; Romo, US20220087755 A1 and US20220304550 A1; Zhang US US20220313375A1; Souper US20210100627 A1; and Schmitz, U.S. Pat. No. 11,033,342 B2.

Other prior art techniques include electroporation. Electroporation is an energy modality of pulsed electric fields in micro and nanosecond domains that, if delivered through a micro-bronchoscope, could be used to deliver genes for immune response, initiate necrosis, or initiate an immunogenic response.

Despite these advances, further advances in this art would be desirable.

BRIEF SUMMARY OF THE INVENTION

Although the systems and methods disclosed herein can be used for many different medical purposes, the present invention was inspired, in part, by a consideration of difficult-to-treat lung diseases and the inadequacies of prior art manual and robotic bronchoscopes.

Thus, this disclosure will discuss both the structure of the lungs and the utility of these improved methods for lung disease in some detail. Note, however, that this extensive discussion of lung structure and improved bronchoscopes is not intended to be limiting. The improved medical devices disclosed herein may be given different names and may be used for a wide variety of medical and veterinary diagnostic and surgical purposes.

About the Structure of the Lung and the Limitations of Prior Art Bronchoscopes

The bronchus of the lungs can be viewed as following a natural Fibonacci pattern of a typical tree where the branches divide and reduce in size as they get further out for the main trunk or, in this case, the Trachea. FIG. 1, which shows the lung bronchus system, shows the size reduction of the bronchial tree as the air moves from the larynx (10), down the Trachea (12), and divides into the Primary Bronchus (14), the Secondary Bronchus (16), the Tertiary Bronchus (18), and lastly the many Bronchiole (20).

The bronchus pathways reduce in diameter as the branches move outward and downward away from the Trachea. For example, going from Subsegmental (Tertiary) to Terminal Bronchi (before the Bronchiole), the diameter usually steps down from about 5 mm (millimeter) down to about 1 mm. This results in about a thousand terminal bronchi that are located in the outer third of the lungs (22). Many lung disorders, such as lung tumors, can occur in this region.

Unfortunately, this outer third portion of the lungs (22) is largely inaccessible to prior art bronchoscopes. This is because prior art bronchoscopes, including robotically driven bronchoscopes, typically have a minimum diameter of 3.5 to 4.2 mm. Such devices are also difficult to maneuver through the many twisting of the bronchial tree because such devices have limited flexibility (e.g., limited or large articulation radii).

Prior art bronchoscopes and robotic bronchoscopes have about a 4 mm diameter and an 18-20 mm articulation radius. These prior art bronchoscopes are typically single-stage catheters, often of continuous diameter, which are introduced into the lung with the aid of an introducer sheath. Occasionally, medical practitioners attach a 19-22 gauge (~1 mm) flexible nitinol needle to the distal tip of the bronchoscope and use this wire tip to reach still further into the lungs for lesion biopsy. However, such wire tips have limited flexibility and maneuverability (limited articulation) and are thus often unsatisfactory for this purpose. At a bronchial diameter of 4 mm, there are roughly 50 bronchi that can be accessed with prior art robotic bronchoscopes. As the bronchial diameter reduces to 3 mm, there are approximately 100 bronchi that can be accessed with a 3 mm robotic bronchoscope, if one existed.

Although not limited to small diameter situations, the invention is based partly on the insight that improved bronchoscopes with diameters below 3 mm can provide a 6 to 20-fold greater opportunity to detect and treat currently unaccessible cancerous lesions in the outer third of the lung. So at 3 mm, we, in effect, have a "biometric transition point" where prior art bronchoscopes fail to proceed further along the ever smaller diameter lung bronchi.

3 mm diameter bronchoscope could access about 100 currently inaccessible bronchi 2.5 mm diameter bronchoscope could access about 300 currently inaccessible bronchi 1 mm diameter bronchoscope could access about 1000 currently inaccessible bronchi The invention is based on further insight that using prior art flexible needles to extend the range is inadequate because such needles are not actively steerable. Such needles have a high risk of tearing through delicate vascular structures because their trajectory will be approximately a straight path when they exit the prior art bronchoscope.

The invention is also based, in part, on the insight that what is needed is an improved bronchoscope, capable of highly narrow distal diameters, as well as an ability to be precision-driven. In some embodiments, this improved device may also utilize an introducer sheath.

FIG. 2 shows a close-up of the various lung bronchus and bronchi pathways, showing the path transition points (104) where a second, narrower stage of a two-stage bronchoscope (100) can extend out from a wider first stage (See FIG. 3). The wider first stage (106) can guide the device through the larger diameter bronchus pathways, and position the narrower second stage (108) to then proceed further through the ever-narrowing segmental bronchi and into the appropriate bronchiole nearest the target (often a potential lesion or tumor).

The challenges of such an improved device should be appreciated. As shown in FIG. 2, the bronchi branches take many sharp turns. For best performance, the improved bronchoscope device needs to articulate and navigate these ever-smaller diameter paths. Thus again, at the Tertiary or Subsegmental Bronchi (3-6 mm diameter, 18), there are about 38 branches. But when the device is traversed beyond the 3 mm Tertiary branches, there are potentially a thousand or more (1000) branches in the Terminal Bronchi (the outer ⅓ of the lungs 22). Ideally, the design would allow the operator to articulate or manipulate the tip of the bronchioscope through each branch without punching through or otherwise damaging the delicate vascular structures and/or bronchus walls.

The invention was also inspired, in part, by the insight that such an improved device should be able to do useful work once it reaches its destination. This includes an ability to robotically position useful sensors, such as cameras and lighting systems, obtain tissue biopsies, and administer effective therapy to tissue targets positioned at such difficult-to-reach locations.

As will be discussed, in some embodiments, the invention teaches robotic, processor-controlled systems and methods of flexing and unflexing various portions of a hollow catheter by using tensioning actuators to create and release tension on various catheter steering cables while also rotating these steering cables in a 1:1 ratio with actuator controlled rotation of different portions of the hollow catheter. This enables the catheter to be driven into hard-to-reach portions of the body while at the same time ensuring that the various steering cables and rotation operations do not interfere with each other.

DETAILED DESCRIPTION OF THE INVENTION

Figure 1:
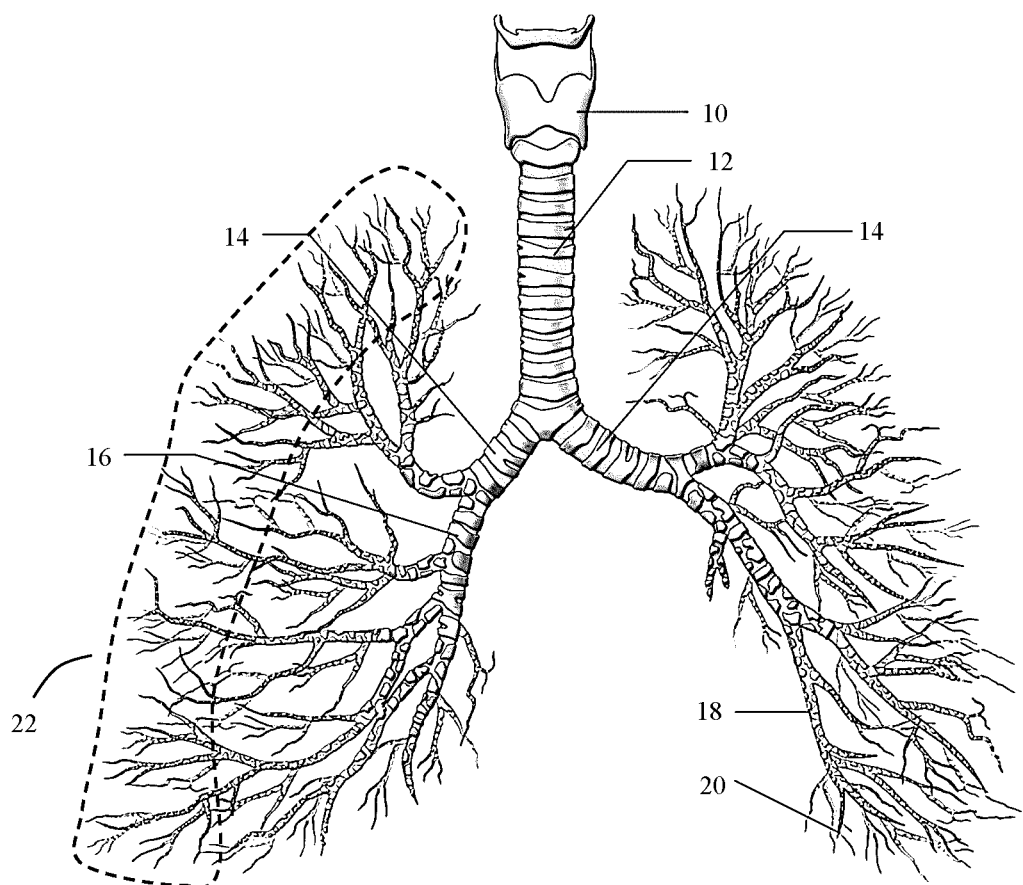
FIG. 1 shows the lung bronchus system.

There is a need to improve surgical procedures by reaching further into various areas of the body with the most minimally invasive approaches. In all instances, the body's internal pathways follow a sequence of narrowing branches. The further down the branch or vessel, the narrower the internal pathway becomes. This creates many challenges for engineers. It pushes the creative and technological limits.

Catheter development is dependent on efficient implementation of metals, polymers, and semiconductors. Metals provide for higher stress limits and thus smaller parts which enable the production of smaller tools. Stainless and Nitinol metals are used in the skeleton of catheters and micromechanical tools. Polymers are used for the skin and insulation of the catheter, allowing smooth interaction between the tool and the body's pathways. Silicon provides the sensing and feedback for producing smart embedded devices at the distal portion of the catheter. Other electronic embedded elements can include video cameras, such CMOS cameras, and LED lighting. The CMOS camera and pico-LEDs provide an important advantage by allowing more flexibility (less resistance) at the distal lead and along the catheter's length. This is due to the braided electrical wires for power, return and communication leads. Whereas fiber optic scopes and fiber optic lighting limit the radius of bend or articulation angle of the catheter due to the higher bending resistance of the glass fibers.

Advances in robotics and visualization systems are creating new opportunities in medicine. These new opportunities create advantages over manual-driven instruments. Stability is one of the advantages, which is easily recognizable when traditional manual surgical tools are attached to the robot. When catheters are robotically driven, several advantages can be leveraged: semi or full-autonomous pathfinding, a locked position, drive methods for traversing further, and tracking position relative to the target with a real-time C-arm surgical imaging device (CT or MRI).

Applying robotics to a catheter exhibits many challenges. Cost and performance must be well balanced due to a disposable cost model. New ideas that approach design for manufacturing (DFM) and cost from the initial challenge push both the creative and technological potentials.

The present invention tackles these challenges by exploiting advanced techniques in micro tool development coupled with robotics and visualization technology.

About nomenclature: in this disclosure, the invention will alternately be described as the invention, the device, the catheter, the bronchoscope, and even the robotically driven articulated bronchoscope. These terms are interconvertible, and using any given term in a specific context is not intended to be limiting.

Description of Applications (Curing Pulmonary Diseases)

Robotic procedures and advances in real-time computer visualization of the body have opened entirely new approaches to targeting and curing many diseases. One such area is in the diagnosis and treatment of lung cancer. Most lung lesions are in the periphery of the lungs. Seventy percent of lung lesions are in the outer third of the lungs. This is a vast opportunity for applying micro-invasive technologies due to narrowing the bronchus in the periphery.

Current detection and treatment are limited by several shortcomings, even with the application of robotics. For robotic bronchoscopy, the catheter technology is limited by the disposable's cost constraints, which directly impacts the catheter size and mobility. Making devices smaller comes with many challenges, which, if not approached carefully, can create cost and performance disadvantages.

These constraints provide a unique opportunity for innovation. Reaching and treating currently inaccessible lesions in the outer third of the lungs is achievable by applying creative manufacturing methods. Developing a highly mobile sub 3 mm robotic micro-bronchoscope that can safely target the outer third of the lungs is desirable. This is an area of the lungs where a thoracic surgeon must apply a biopsy needle under fluoroscopy by going transthoracic to obtain a tissue sample. Although this is the standard of care for the hard-to-reach areas of the lungs, it comes at a price with a pneumothorax rate of 20%. Additionally, this procedure does not provide a targeted treatment or cure if the lesion is cancerous. It is only a diagnostic method. The cost of treating a 20% pneumothorax rate is a huge issue and a great opportunity for developing better treatment methods.

The outer third of the lungs (22) is where 70% of lung lesions are located. Going transluminal from the bronchus to the outer third provides the opportunity to biopsy (detect) and treat the lesion (if found to be cancerous) during the same procedure. In addition to detecting and treating cancer, other illnesses, such as chronic bronchitis, could be treated with electroporation to elicit an immunogenic response. Another application would be targeted micro-lung-lavage at the Alveoli.

Figure 2:
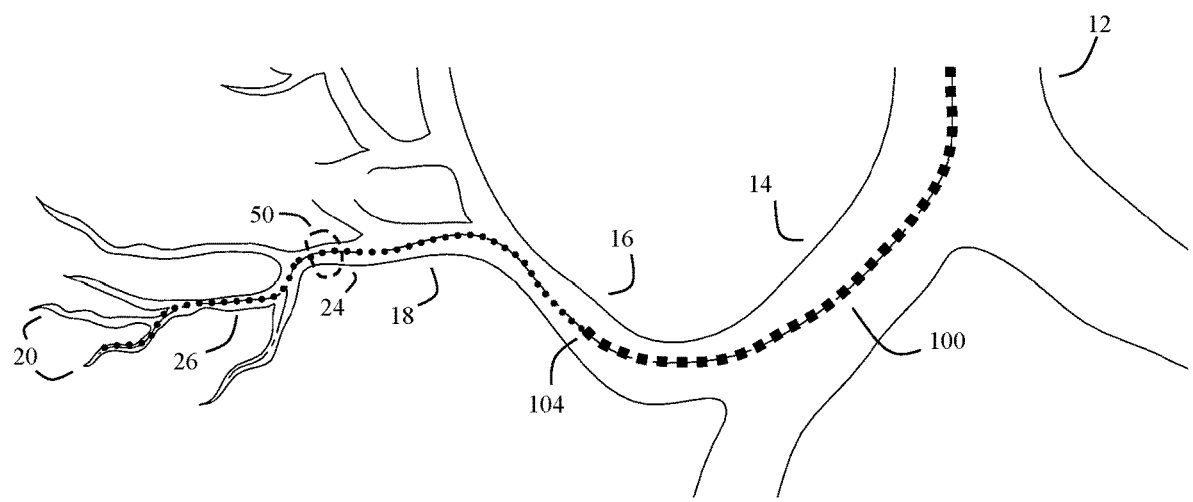
FIG. 2 shows the various bronchi structures and pathways

FIG. 2 shows the trajectory paths from Primary (14) to Secondary (16) and then at the end of the Tertiary branch (18), where the pathway narrows to <3 mm in the subsegmental Bronchi. This is the transition to Terminal Bronchi. The thick dashed or broken line represents the path of a Bronchoscope (100). Along the scope's path, transition points are labeled. These points are labeled "End of Introducer Path" (104), "End of Proximal Path" (24), "Biometric Transition Point" (50), and "Distal Stage Path" (26). These labels represent some of the key areas along the length of the endoluminal catheter disclosed in this application.

As previously discussed, prior art robotic bronchoscopes have a diameter of about 4 mm and also have about a 18-20 mm articulation radius (turning radius). Although, in some prior art situations, a 19-22 gauge (~1 mm diameter) flexible nitinol needle can be attached to the tip of the bronchoscope for lesion biopsy, such needles are difficult to steer and tend to be unsatisfactory for many purposes.

Figure 3:
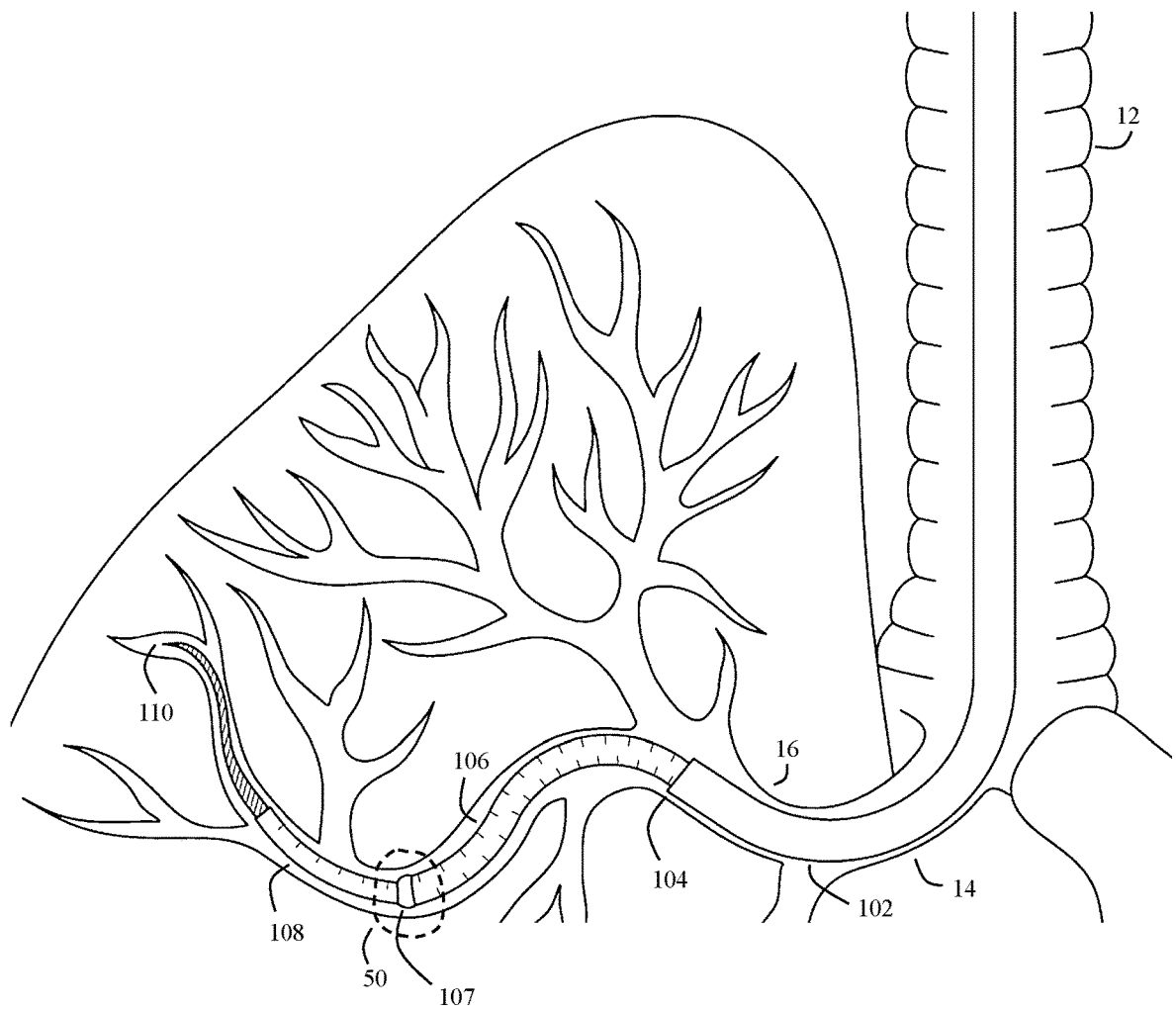
FIG. 3 shows a hypothetical path for the invention's bronchoscope reaching the outer ⅓ of a lung.

Based on the trajectory path in FIG. 2 and FIG. 3, the "Biometric Transition Point" (50) can be viewed as the region of the lungs with bronchus and bronchi diameter of 3 mm or less, where prior art bronchoscopes stop.

As previously discussed, in some embodiments, the invention may be a bronchoscope with at least one stage and an optional introducer sheath (102) where the one or more stages (106) and (108) are robotically driven along the same axis. FIG. 3 shows a close-up of the path transition points where a two-stage bronchoscope may be divided (based on biometric data).

This is the challenge, especially where the bronchi branches take sharp turns. The narrowing of pathways below 3 mm diameter (50) creates a huge opportunity for an improved bronchoscope that can articulate and navigate these smaller diameter paths. For Tertiary or Subsegmental Bronchi (3-6 mm), there are 38 branches. When the bronchoscope is traversed beyond the 3 mm Tertiary branches (50), the opportunity rises to 1000 branches in the Terminal Bronchi (the outer third of the lungs 22). Beyond the Tertiary branches, this can be viewed as being a biometric transition in the design of the two-stage bronchoscope. The improved device and methods disclosed herein may, in some embodiments, be designed to penetrate this (3 mm diameter or less) region of the lungs (22) through reduced size and improved maneuverability. This allows the device to reach regions that are generally inaccessible to prior art manual or robotic bronchoscopes.

FIG. 3 shows the four main components of a two-stage embodiment of the improved catheter system: These are the introducer sheath (102), the proximal stage (106), the distal stage (108), and the probe or tool (110). At (107), there is an optional isolation transition coupler or junction where the proximal stage (106) is coupled or bonded, welded, or snaped together to the distal stage (108). As can be seen in FIG. 3, the distal stage (108) may have a much smaller outer diameter (OD) than the proximal stage (106). The device can be configured so that the surgeon or robot can manipulate the primary stage (106) and coupler, junction, or transition region (107) near the biometric transition point (50) and then use the distal stage (108) to proceed further into the outer third of the lungs (22) or other difficult to access region.

In a preferred embodiment, the surgeon, with or without robotic assistance, will often manipulate (106), (107), and (108) in synchrony to get to a desired location near the target. Then, a tool or probe, such as (110), may slide out and extend to the target.

Thus, in some embodiments, the invention may be a one- or more-stage catheter device for traversing internal body passages, this at least one-stage catheter device comprising a distal hollow catheter portion and a similar or different proximal hollow catheter portion. In the case where the invention is a one-stage catheter device, with the distal and proximal sides of the catheter being the same material, these sides will be termed the distal and the proximal portions. In the case where the invention is a multi-stage catheter device with at least two stages, the distal side will be referred to as the distal stage, and the proximal side (which may be of a different material or dimensions) will often be referred to as the different proximal stage. In cases where it doesn't matter if we are talking about a catheter portion or stage, the term "stage/portion" may be used.

Considering the two-stage embodiment first, in this embodiment, the different proximal stage hollow catheter (106) comprises a hollow torque shaft (200). Here, one end of the distal stage hollow catheter (108) is affixed to an end of the hollow torque shaft (200) by either a junction, such as a region where the two sides are bonded, welded, or snaped together to each other (107j), or by an isolation transition coupler (107, 107a, 107a1, 107a2). The junction (107j) will generally have the same diameter as the larger of the two sections. If an isolation transition coupler, it may be configured (e.g., with an appropriate external diameter) to traverse an internal body passage (i.e., the objective internal body passage for that particular medical procedure).

This isolation transition coupler (107, 107a, 107a1, 107a2) generally comprises a hollow cylindrical housing with at least one distal coil stop (107b). As previously discussed, the isolation transition coupler (107, 107a, 107a1, 107a2) is configured to act as a joint between one end (e.g., the proximal end) of the distal stage hollow catheter (108) and (the distal end of the) hollow torque shaft (200, 106). This joint acts to couple the two stages so that torque applied to the (proximal) hollow torque shaft (200) is conveyed to the distal stage hollow catheter (108).

The at least one-stage device further comprises at least one steering cable type conduit (such as 220) that extends along the catheter from the proximal stage (often from the proximal end of the proximal stage) to the distal stage (often to the distal end of the distal stage). In some embodiments, at least one of these steering cables will comprise both a (steering) cable (220) and a surrounding isolation coil (380). In either case, the steering cable, with or without a surrounding isolation coil, will often be termed a "tensioning cable." Thus, some "tensioning cables" may have isolation coils, and some may not. Further description (i.e., drawings or text indicating if a particular steering cable/tensioning cable has an isolation coil) will help distinguish. In the absence of further description, then both options may be used.

For those tensioning cables comprising a steering cable (220) and a surrounding isolation coil (380), such tensioning cables will connect to their respective distal coil stop (107*b*) so that this particular distal coil stop acts as an isolation coil stop to prevent further distal movement and progression of the isolation coil (380). At the same time, the distal coil stop (107*b*) is configured (often with a suitable central hole 107*c*) so that the internal steering cable (220) itself can pass through the distal coil stop (107*b*). In other words, at the distal coil stop, further distal movement of the surrounding isolation coil (380) is blocked, but further distal movement and progression of the internal steering cable (220) is permitted.

The catheter device may also be configured so that the hollow torque shaft, distal stage hollow catheter, and the isolation transition coupler further comprise a working channel (228). This working channel is configured to convey at least one other type of conduit (230, often a different type of conduit other than a steering cable 220) through the proximal stage/portion hollow catheter and the distal stage/portion hollow catheter, often to at least a distal tool plate (109) mounted on a distal end of the distal stage/portion hollow catheter (108). Alternatively, one or more steering cables (220) can be adhered or welded to the end of the catheter (108).

Note that at least one of the tensioning cables comprises at least one distal stage steering cable (220) that is often connected (220*t* affixed) to the distal tool plate (109). This at least one distal stage steering cable is configured to convey distal stage steering force to the distal tool plate (109), causing the distal tool plate and the distal stage catheter to move or bend according to the distal stage steering force.

Figure 4A:
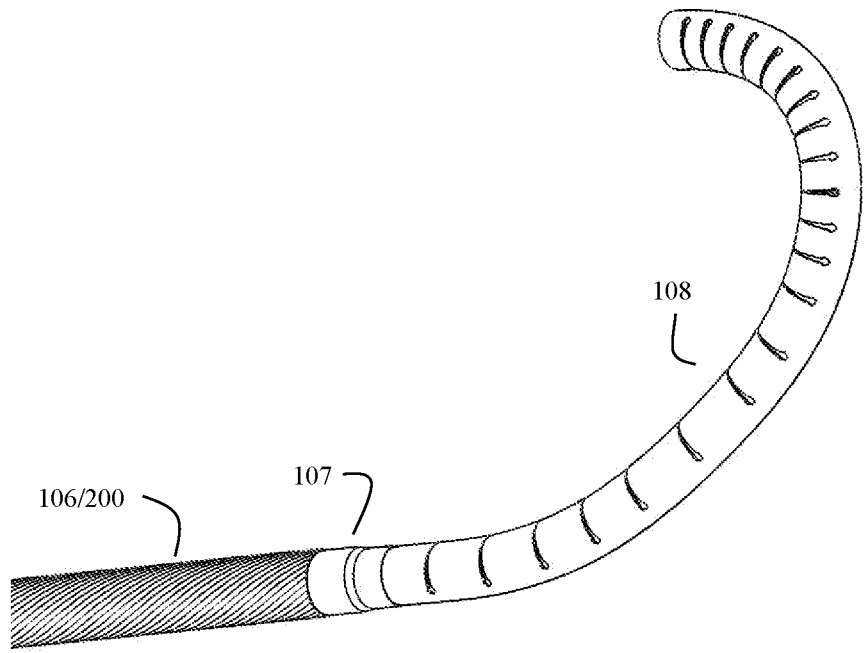
FIG. 4A shows the distal end of the invention's catheter device, showing the distal end may comprise a highly flexible articulable distal section, an optional isolation transition coupler, and a proximal portion comprising a torque shaft or tube.

FIG. 4A shows the distal end of the invention's simplified, highly maneuverable catheter device, showing the distal end comprises a highly flexible articulable distal section (108), an optional isolation transition coupler (107), and a proximal portion (106) comprising a torque tube (200).

Figure 4B:
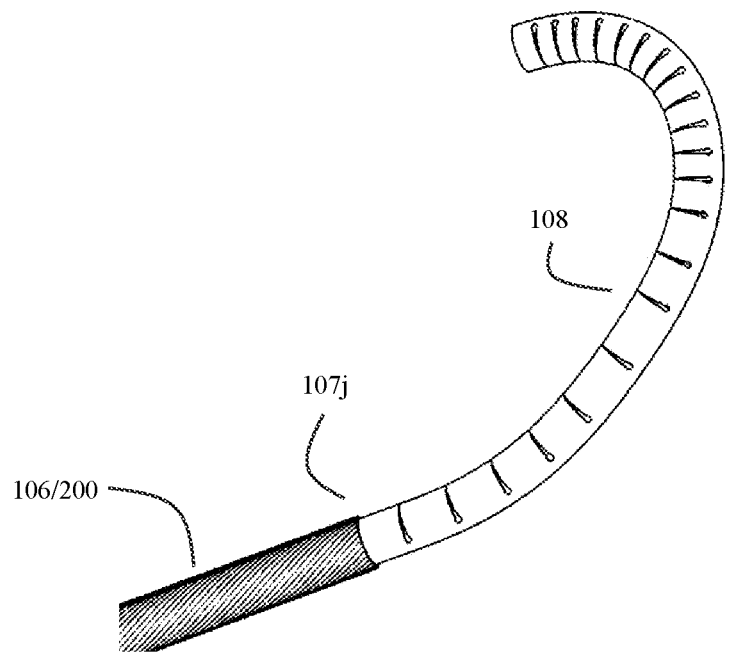
FIG. 4B shows the distal end of an alternate embodiment of the invention's catheter device. Here, the catheter comprises a highly flexible, articulable distal stage joined (often by bonding or welding) to a proximal stage comprising a torque shaft or tube. There is no isolation transition coupler, but the two stages are distinct.

FIG. 4B shows the distal end of an alternate embodiment of the invention's catheter device. Here, the catheter comprises a highly flexible, articulable distal stage (108) joined to a proximal stage comprising a torque shaft or tube (106/200) at a junction (107*j*). There is no isolation transition coupler, but the two stages are distinct.

Figure 4C:
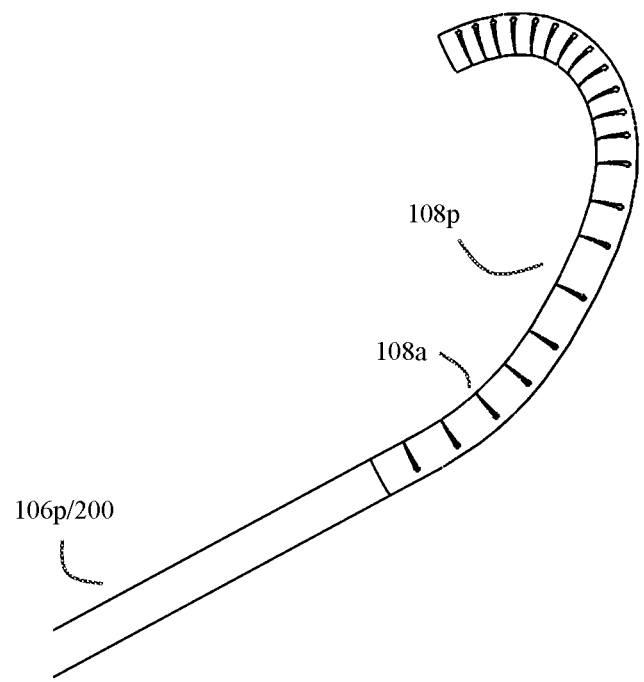
FIG. 4C shows the distal end of another embodiment of the invention's catheter device. Here, the catheter comprises a highly flexible, articulable distal portion that is continuous with a proximal portion configured to act as a torque shaft or tube. There is no isolation transition coupler. The two portions are made of the same material, so no joint or junction is needed, but here, the distal portion is shown with a plurality of slits for greater maneuverability. The slits can be of any pattern that allows for flexure. In place of the slits, this could be a multi-durometer polymeric material with a stiffer backside and softer (lower durometer) inside (inside highly flexible area) where the cable pulls to compress this softer material.

FIG. 4C shows the distal end of another embodiment of the invention's catheter device. Here, the catheter comprises a highly flexible, articulable distal portion (108*p*) joined to a proximal portion (106*p*), here configured to act as a torque shaft or tube (100). There is no isolation transition coupler and no junction. The two portions are made of the same material, but here, the distal portion has a plurality of slits for (108*a*) greater maneuverability. The slits can be of any pattern that allows for flexure. In place of the slits, this could be a multi-durometer polymeric material with a stiffer backside and softer (lower durometer) inside (inside highly flexible area) where the cable pulls to compress this softer material.

Figure 5A:
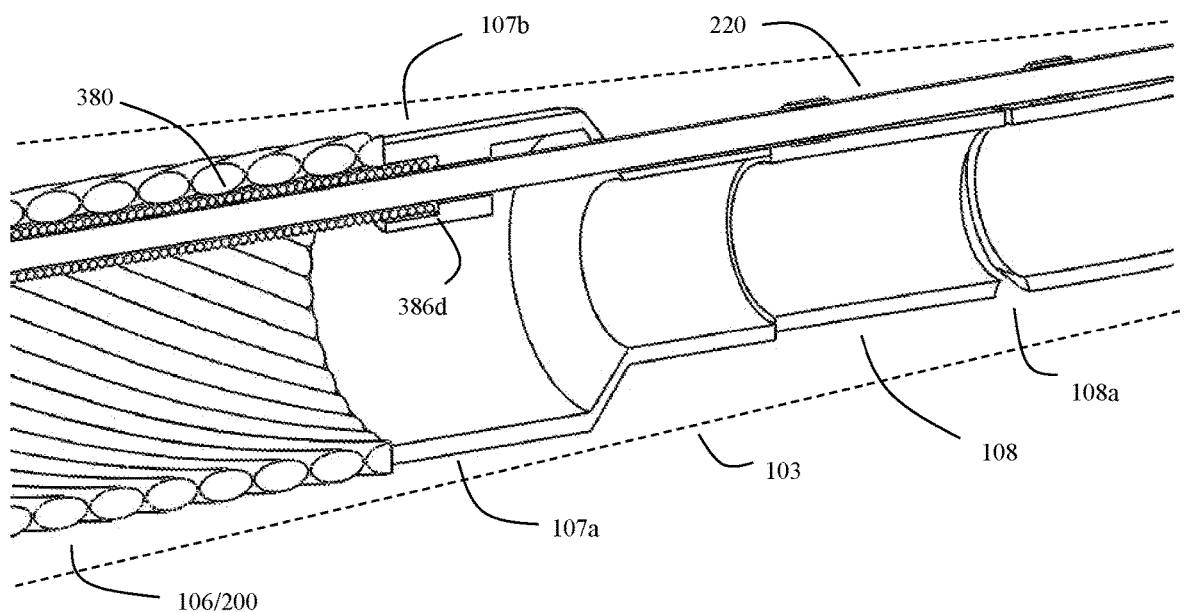
FIG. 5A shows a cross-section of one embodiment of the catheter. In this embodiment, the proximal portion of the cable is disposed inside the proximal portion of the catheter, and the distal portion of the tension cable is disposed along the exterior of the distal portion of the catheter.

FIG. 5A shows a cross-section of one embodiment of the catheter where the proximal portion of the tension cable (220, 380) is disposed inside the proximal portion of the catheter (106/200), but the distal portion of the tension cable (i.e., steering cable 220) is disposed along the exterior of the distal portion of the catheter (108).

Figure 5B:
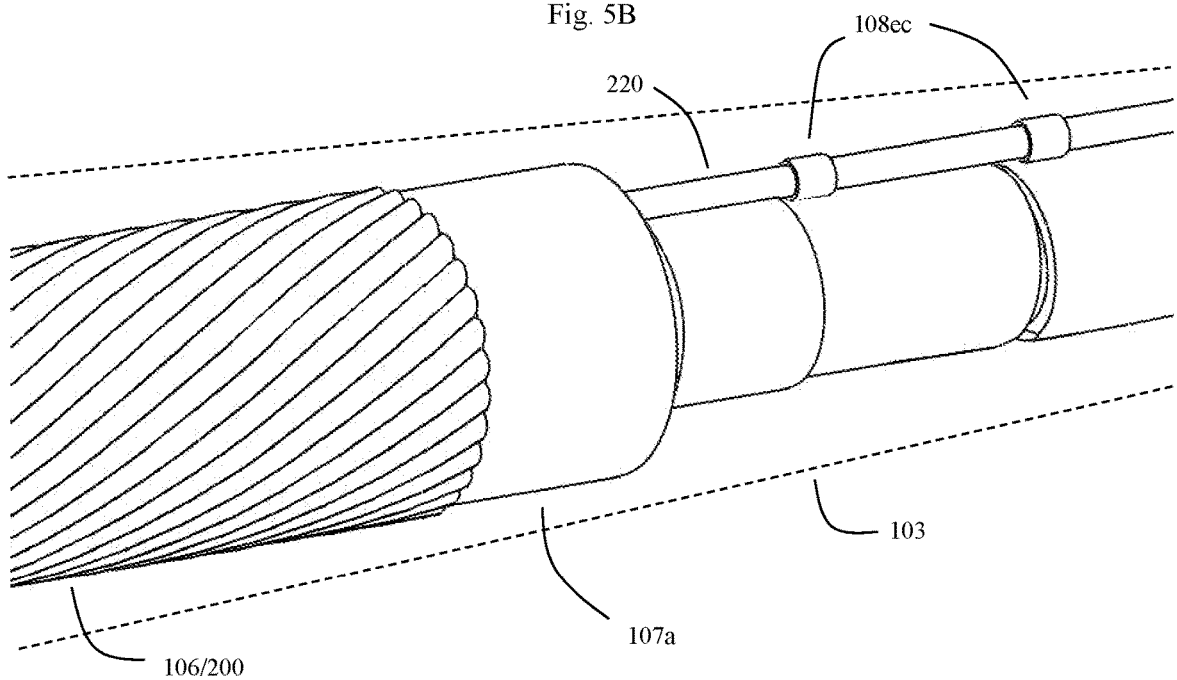
FIG. 5B shows the exterior of the catheter device previously shown in FIG. 5A.

FIG. 5B shows the exterior of the catheter device previously shown in FIG. 5A.

In this embodiment, the proximal side (108) torque shaft (200) is affixed to the distal stage (106) by way of an isolation transition coupler (107). This isolation transition coupler (107) will usually comprise a housing (107*a*) and at least one isolation coil stop (107*b*). The catheter will further comprise at least one steering cable (220).

As previously discussed, in some embodiments, this steering cable (220) is covered by a surrounding isolation coil (380) as the cable progresses up the proximal portion of the catheter until the isolation coil (380) encounters the isolation coil stop (107*b*). At the isolation coil stop, the further distal motion of the isolation coil is blocked, but the steering portion of the tensioning cable (220) itself can progress distally (often through a hole 107*c* in the isolation coil stop) and up the distal portion of the catheter (108), usually, until it hits an anchor point (220*t*) at the distal tool plate (109). See FIG. 9 and FIG. 12A, FIG. 21 (220). In some embodiments, the catheter may be further covered by an optional flexible polymer jacket (103).

This flexible polymer jacket (103) often differs from the optional sheath (102). The polymer jacket may comprise a biocompatible polymer selected to cushion and facilitate the passage of the catheter through narrow body openings. Examples of suitable polymers include hydrogels such as Pluronic (F127)/acrylic acid (AA) hydrogels, and the like.

More specifically, in some embodiments, any of the distal stage hollow catheter (108), proximal stage hollow catheter (106/200), and isolation transition coupler (107, 107*a*, 107*a*1, 107*a*2) may be surrounded on their exterior surfaces by a flexible polymeric jacket (103) which may be either continuous or discontinuous between sections.

Figure 5C:
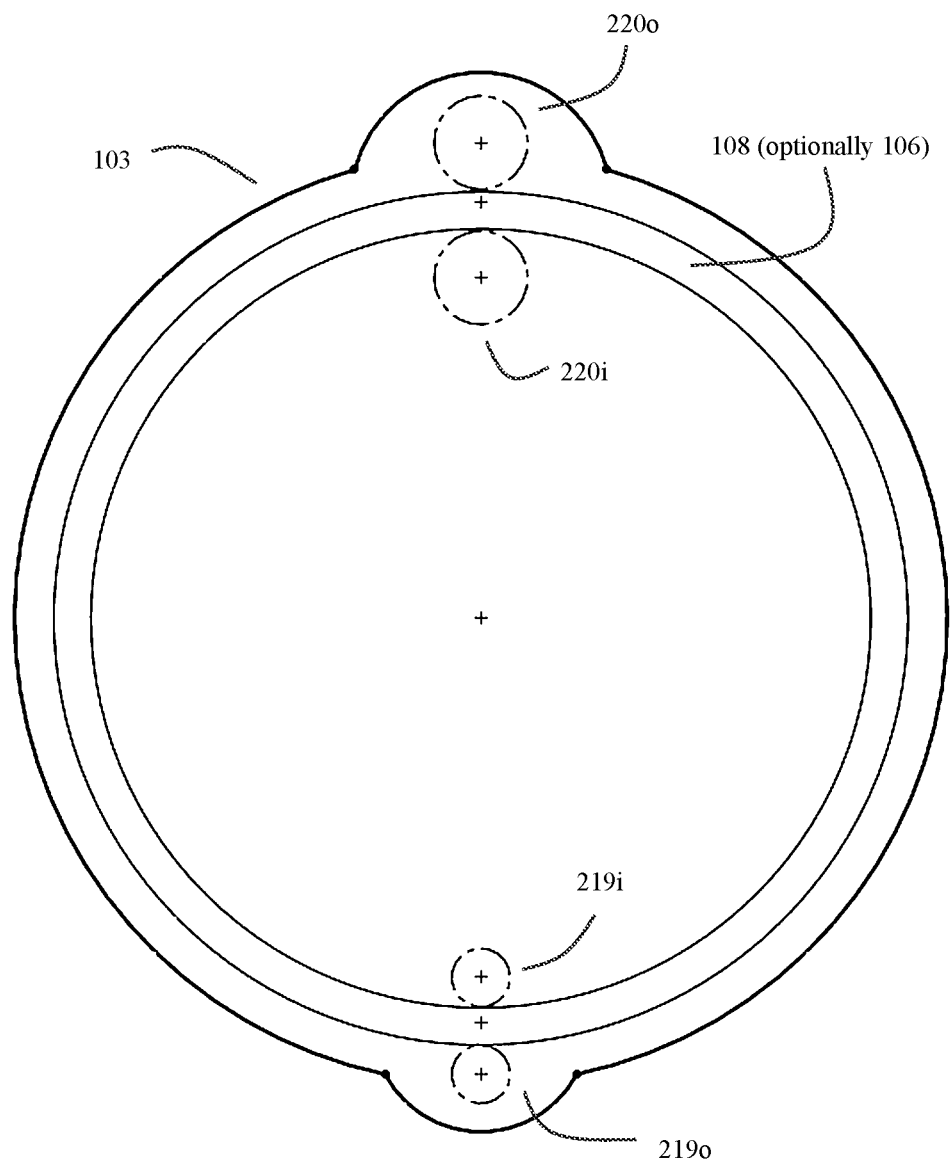
FIG. 5C shows a cross-section of an alternate embodiment of the system employing an optional polymer jacket with spring/elastic-return features configured to oppose the force exerted by the tensioning cable(s).

In some embodiments, as shown in FIG. 5C, the device may further comprise at least one elastic (219*i* or 219*o*) "or spring" element configured to oppose forces applied by at least one of said at least one tensioning cable (220). (Here 2200 is a tensioning cable positioned outside of the catheter, optionally in or under a polymeric jacket, while 220*i* is a tensioning cable positioned inside the catheter.) This elastic element will often be positioned on the side of the catheter 180 degrees, opposite to the tensioning cables (220) that the elastic element is intended to counteract. (other angles are also possible and may be desirable if a slight catheter curve is desired). In some embodiments, one or more elastic elements may form a part of the flexible polymeric jacket. These elastic elements may be springs or spring materials such as nitinol, elastic polymer ligaments, or other elastic materials In these embodiments, the polymeric jacket (103) may have properties (elastic elements 219*i* or 219*o*) that cause the flexible portions of the catheter to return to a straight or other desired curvature once tension is released. These elastic elements could be a thicker elastic section, or a spring wire embedded in or under (219*o*) the elastic jacket. There could also be elastic biasing internally, such as a spring wire (219*i*), positioned inside the catheter 108 (or 106) that causes the catheter to return to straight or other desired curvature once tension is released.

FIG. 5C shows a cross-section of an alternate embodiment of the system employing this optional polymer jacket with spring/elastic-return features configured to oppose the force exerted by the tensioning cable(s).

Note that as previously discussed, in the embodiment shown in FIGS. 5A and 5B, the steering cable (220), as well as the surrounding isolation coil (380), first progresses along the interior of the torque shaft (200). However, further progress of the isolation coil (380) is blocked at the isolation coil stop (107b), and the tensioning cable/steering cable (220) then progresses through a hole in the isolation transition coupler (see FIG. 5B, 107c), and then along the exterior of the distal portion of the catheter (108). Here the steering cable (220) may optionally be held into position by various exterior clips (108ec). Note that these clips are loose enough to enable the steering cable (220) to move along the axis of the catheter but tight enough to hold the steering cable relatively close to the exterior side of the distal portion of the catheter (108). The clips 108ec are attached by bonding, welding, clipped, snap fit, formed or pushed out of tube 108.

Note the distinction between the far distal end isolation coil (386d) and the isolation coil stop (107b). The far distal isolation coil end (386d) is where the isolation coil (380) ends on the distal side. By contrast, the isolation coil stop (107b) is the physical feature on the isolation transition coupler (107b) that prevents this isolation coil (380) from moving further in the distal direction.

Figure 6A:
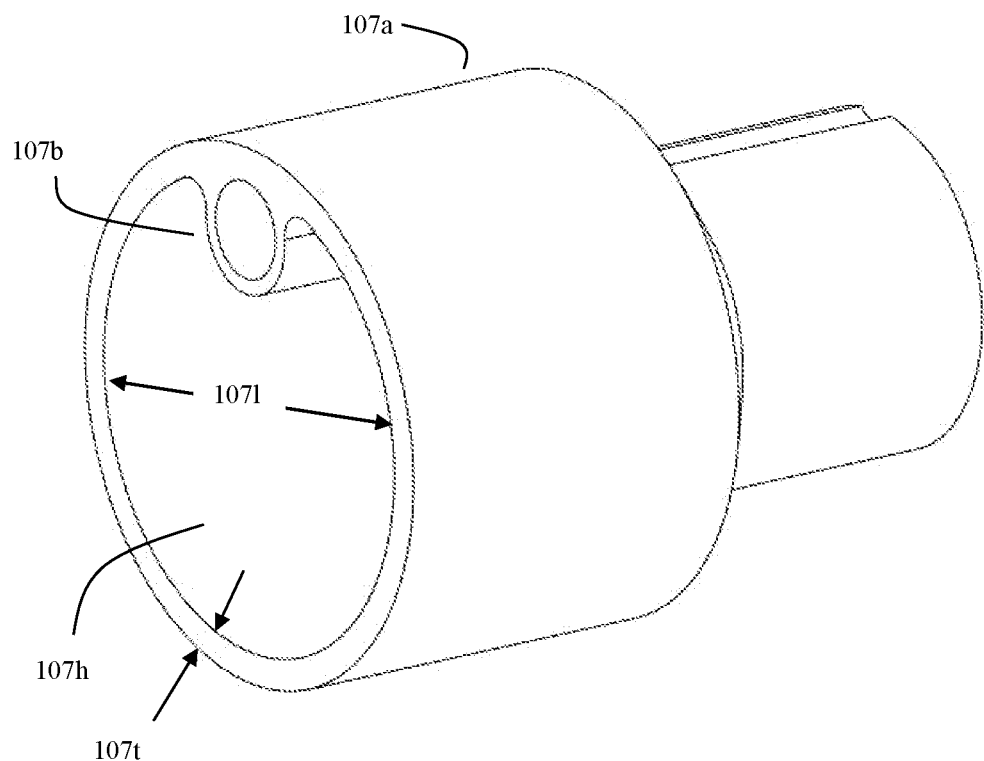
FIG. 6A shows a close-up of the first side of the optional isolation transition coupler previously shown in FIG. 5A and FIG. 5B.

FIG. 6A shows a close-up of one side of one embodiment of the isolation transition coupler (107a), showing the hollow interior (107b) and a detail of the front end of the distal coil stop (107b). Here the internal diameter of the larger side is shown as (107l). The thickness of the isolation transition coupler shell is shown as (107t). The external diameter of this portion is thus (107l)+2*(107t).

Figure 6B:
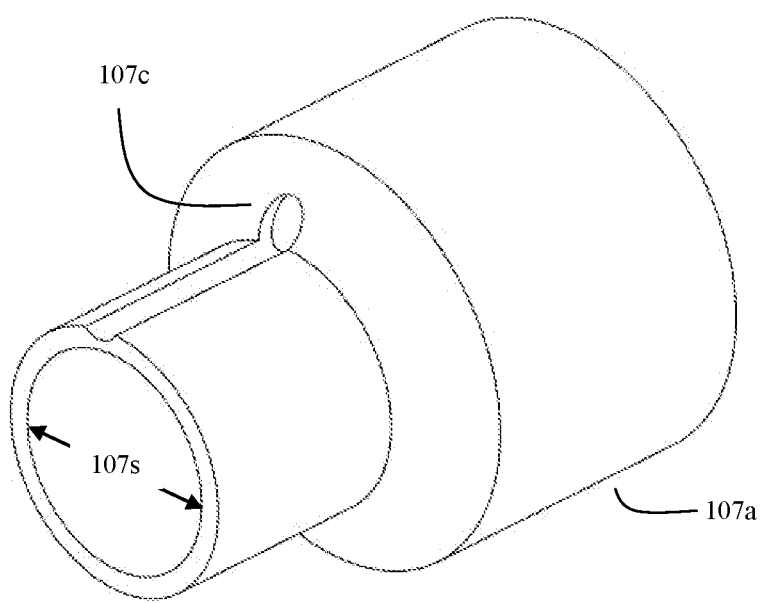
FIG. 6B shows a close-up of the other side of the optional isolation transition coupler previously shown in FIG. 5A and FIG. 5B.

FIG. 6B shows a close-up of the opposite side of this embodiment of the isolation transition coupler (107a), showing the exit hole (107c) by which the tensioning cable (220) can exit the distal coil stop. There the internal diameter of the smaller side is shown as (107s). Assuming that the thickness of the isolation transition coupler shell in this region is also (107t), then the external diameter of this portion is thus (107s)+2*(107t). Usually, the thickness of the transition coupler shell (107t) is less than 10 to 20 percent of (107l) or (107s).

The thickness of the isolation transition coupler wall (107t) is usually similar to the thickness of the catheter's proximal portion (106/200) and a distal portion (106), which in turn is usually less than 20 percent of the internal diameters (107s and/or 107l).

Note that the distal stage hollow catheter is usually tapered from a larger diameter (107l) at the proximal end of the isolation transition coupler to a smaller diameter (107s) at the distal end of the distal stage hollow catheter. In general, the device is configured to enable at least distal portions of the distal stage hollow catheter to be maneuvered through body lumens with internal open diameters of 3 millimeters or less. Thus, the sum of the dimensions of (107l)+2 times (107t) may often be 3 millimeters or less.

Figure 7A:
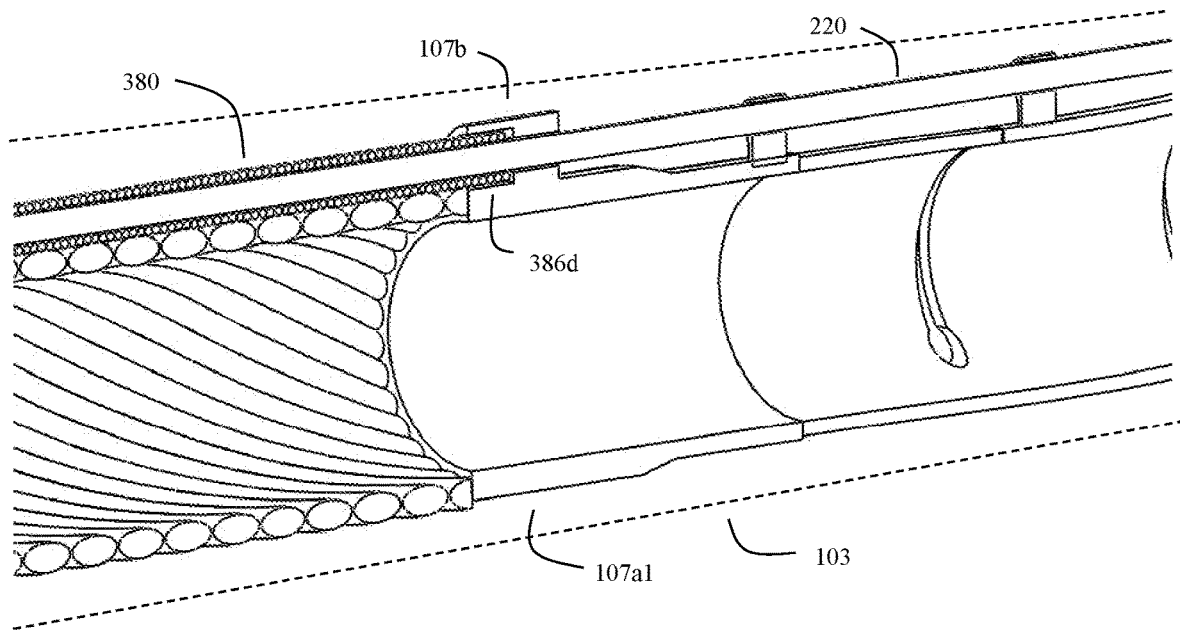
FIG. 7A shows a cross-section of a different embodiment of the catheter, where the proximal portion of the tension cable is disposed outside the proximal portion of the catheter, and the distal portion of the tension cable is also disposed along the exterior of the distal portion of the catheter.

FIG. 7A shows a cross-section of a different embodiment of the catheter where the proximal portion of the tension cable (220) is disposed outside the proximal portion of the catheter, and the distal portion of the tension cable (220) is also disposed along the exterior of the distal portion of the catheter. This version of the isolation transition coupler (107a1) lacks the exit hole (107c) previously shown in FIG. 6B. In this version, the distal coil stop (107b) is located on the outside of the isolation transition coupler. For this reason, this variant of the isolation transition coupler is here shown as (107a1), but otherwise will still be termed an "isolation transition coupler," and designations of (107 and 107a) are generally intended to refer to this variant as well.

Figure 7B:
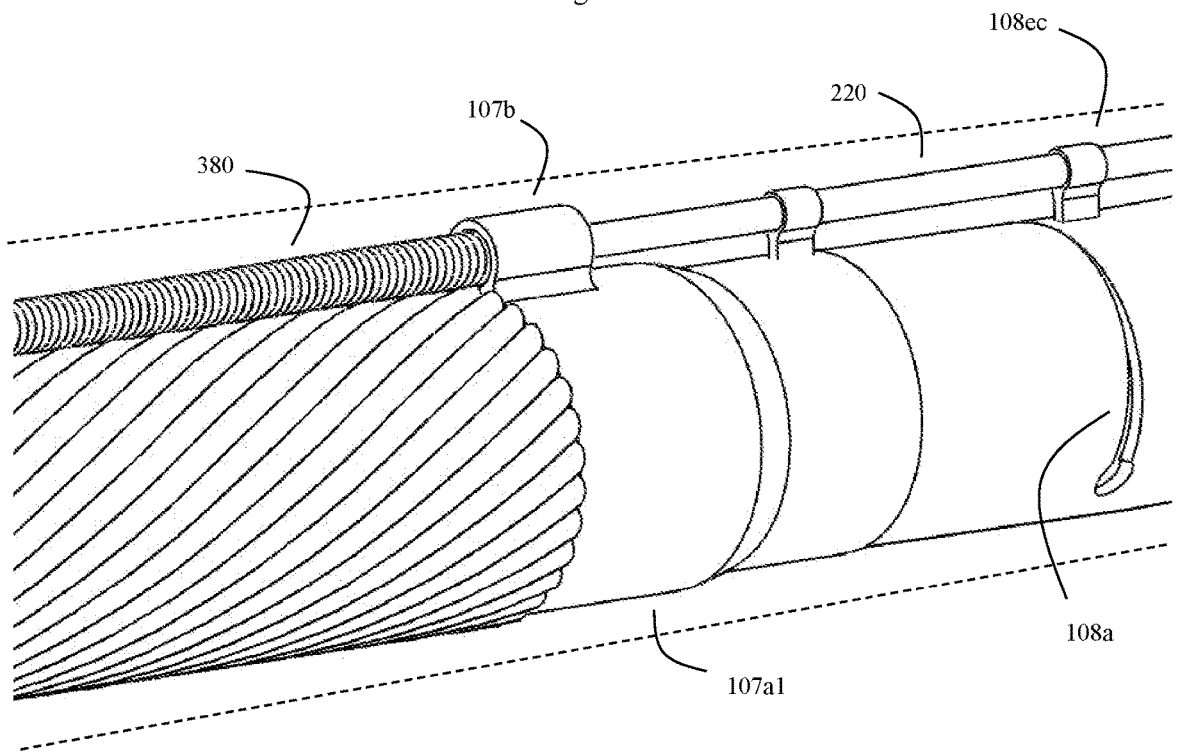
FIG. 7B shows the exterior of the catheter device previously shown in FIG. 7A.

FIG. 7B shows the exterior of the catheter device previously shown in FIG. 7A.

To expand on isolation coils: As previously discussed, in some embodiments, portions of at least one distal stage steering cable (220) are further disposed inside an isolation coil (380). This isolation coil (380) comprises a far-isolation-coil-end (FIG. 5A, 386d) and a near-isolation-coil-end (FIG. 28B, 382n). In this embodiment, each far-isolation-coil-end is attached proximate to a distal terminus of its corresponding steering cable (220) in a manner that allows the corresponding steering cable (220) to movably protrude past the far-isolation-coil-end (386d) while blocking the axial movement of the far-isolation-coil-end.

Further, each near-isolation-coil-end (382n) is attached proximate to its respective flexing actuator in a manner that allows the corresponding steering cable (220) to movably protrude past the near-isolation coil end (382n) while blocking axial movement of the near-isolation-coil-end.

Figure 11:
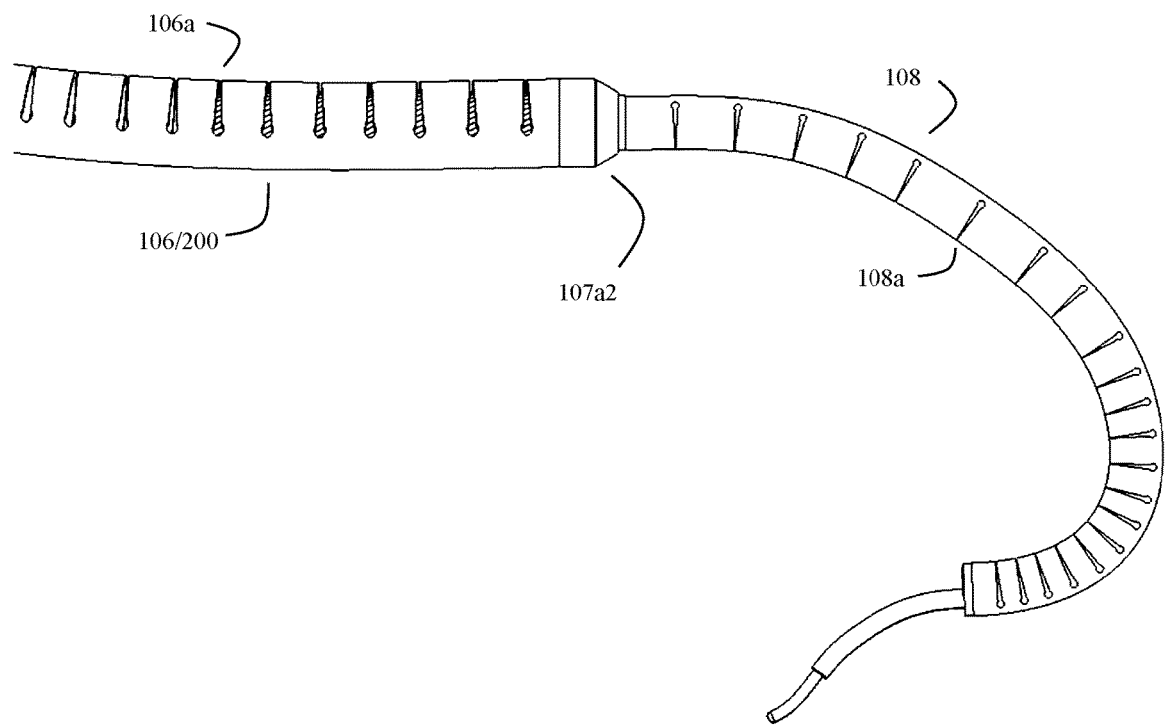
FIG. 11 shows how the flexible sections can be tailored to a patient's particular bronchi, where the lesion location may be a more challenging area to reach due to some non-conformity

FIG. 7 and FIG. 11 also show that at least the distal stage hollow catheter (108), and often the proximal stage hollow catheter (106/200) will often comprise a plurality of slits (106a, 108a) along at least a portion of their circumference. The slitted shaft for 106/200 is functional for both flexing and transmitting torque. These slits are configured to have positions and dimensions to facilitate traversal of the catheter device through a series of branching body lumens of progressively smaller internal diameters, such as shown in FIG. 3.

Indeed, note that in some embodiments, any of the distal stage/portion and the proximal/stage portion comprise any of a woven, non-woven, or continuous material with a plurality of slits or openings along at least a portion of their circumference. In general, this material will be selected to have positions and dimensions configured to enable the device to travel through a series of branching body lumens of progressively smaller internal diameters.

Figure 8:
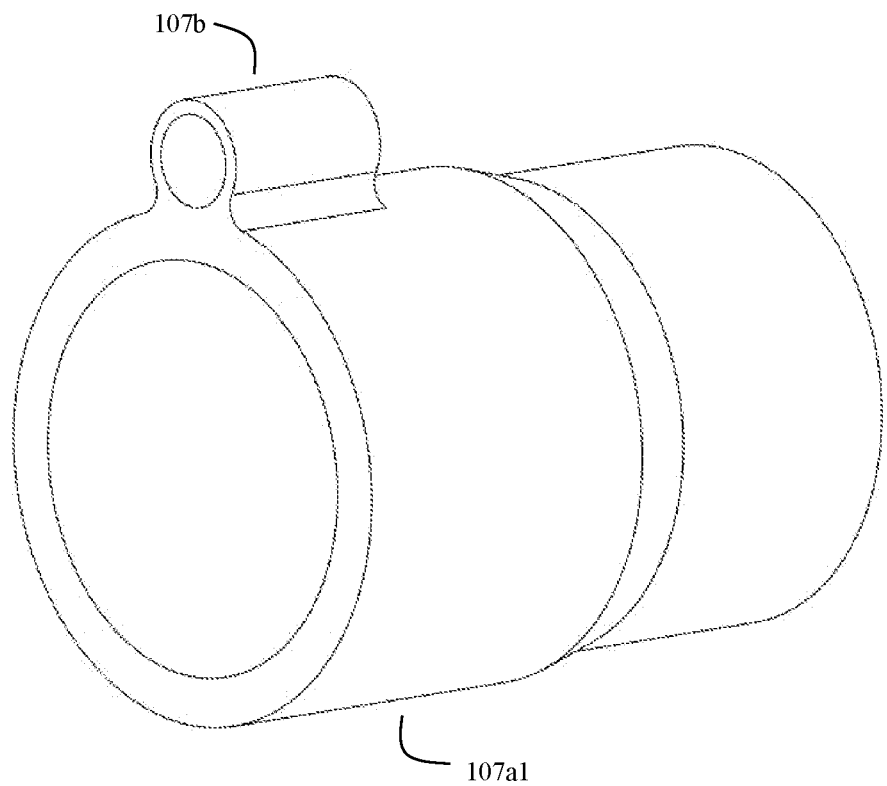
FIG. 8 shows a close-up of the optional isolation transition coupler previously shown in FIG. 7A and FIG. 7B.

FIG. 8 shows a close-up of the optional isolation transition coupler (107a1) previously shown in FIG. 7A and FIG. 7B.

Figure 9:
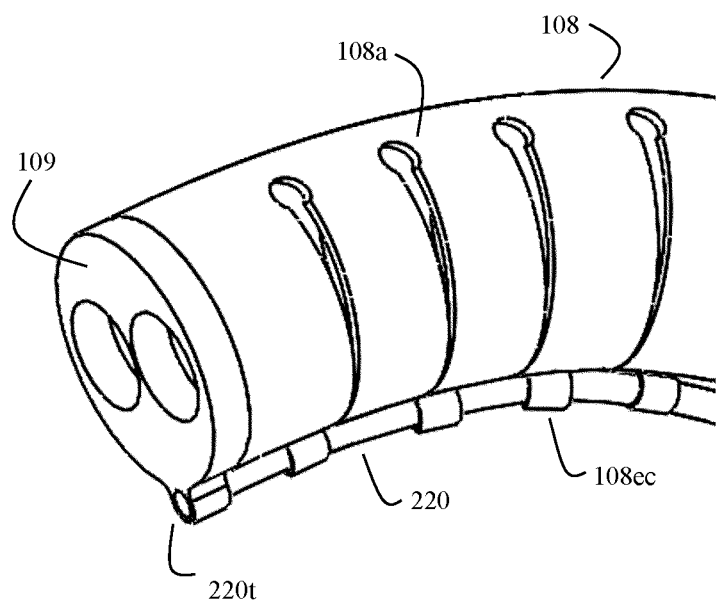
FIG. 9 shows a detail of the extreme distal end of the catheter where the tension cable is disposed outside of the distal catheter.

FIG. 9 shows a detail of the extreme distal end of the catheter. In this embodiment, the steering cable (220) end of the tensioning cable terminates at the distal plate (109). It is terminated by being connected (e.g. adhered, gipped, welded, glued) at the termination region (220t). As a result, force or tension on this steering cable (220) end of the tensioning cable will cause the distal end of the catheter to bend in the direction of the applied force. As previously discussed, in some embodiments, there may be multiple steering or tensioning cables (See FIG. 14, 220, 222, 224, 226) configured to cause the distal end of the catheter to bend in multiple directions depending on the applied force. Each direction of bending is occasionally referred to as a "way", such as 1-way, 2-way, and so on.

Figure 10A:
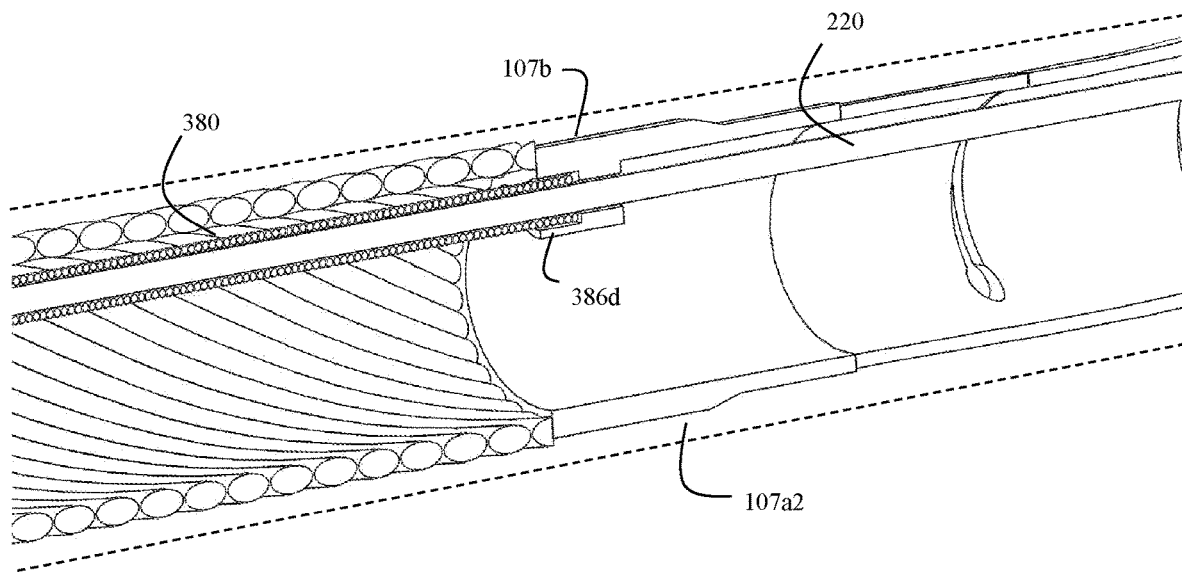
FIG. 10A shows a cross-section of a different embodiment of the catheter where both the proximal portion of the tension cable is disposed along the interior of the proximal portion of the catheter, and the distal portion of the tension cable is also disposed along the interior of the distal portion of the catheter.

FIG. 10A shows a cross-section of yet another embodiment of the catheter where both the proximal portion of the tension cable is disposed along the interior of the proximal portion of the catheter, and the distal portion of the tension cable is also disposed along the interior of the distal portion of the catheter. This version of the isolation transition coupler also lacks the exit hole (107c) previously shown in FIG. 6B, and the distal coil stop (107b) is located inside the isolation transition coupler. For this reason, this variant of the isolation transition coupler is here shown as (107a2), but otherwise will still be termed an "isolation transition coupler," and designations of (107*a*) are generally intended to refer to this variant as well.

Figure 10B:
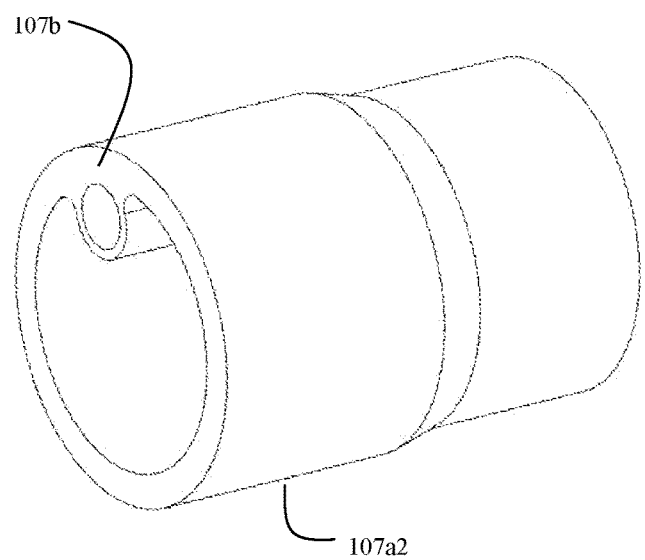
FIG. 10B shows a close-up of the optional isolation transition coupler previously shown in FIG. 10A.

FIG. 10B shows a close-up of the optional isolation transition coupler (107*a*2) previously shown in FIG. 10A.

Figure 10C:
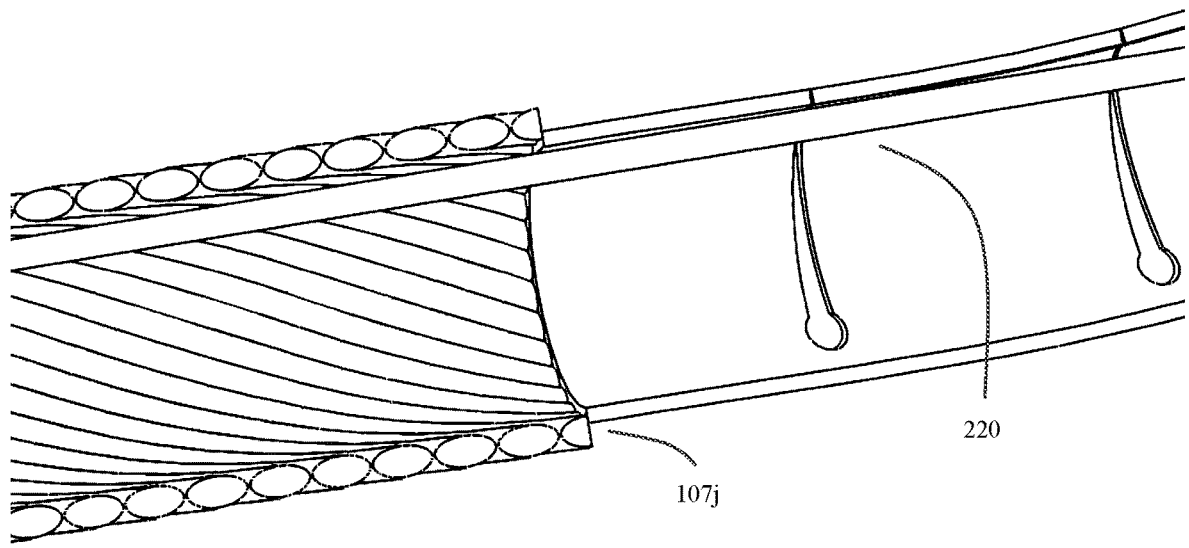
FIG. 10C shows a cross-section of an alternative embodiment of a two-stage catheter, where the distal stage is affixed to the end of the proximal stage by a junction. In this embodiment, the tension cable lacks an isolation coil and also lacks an isolation transition coupler.

FIG. 10C shows a cross-section of an alternative embodiment of a two-stage catheter where the distal stage is affixed to the end of the proximal stage by a junction (107*j*). There is no isolation transition coupler. In this embodiment, the steering cable/tension cable (220) lacks an isolation coil.

Figure 10D:
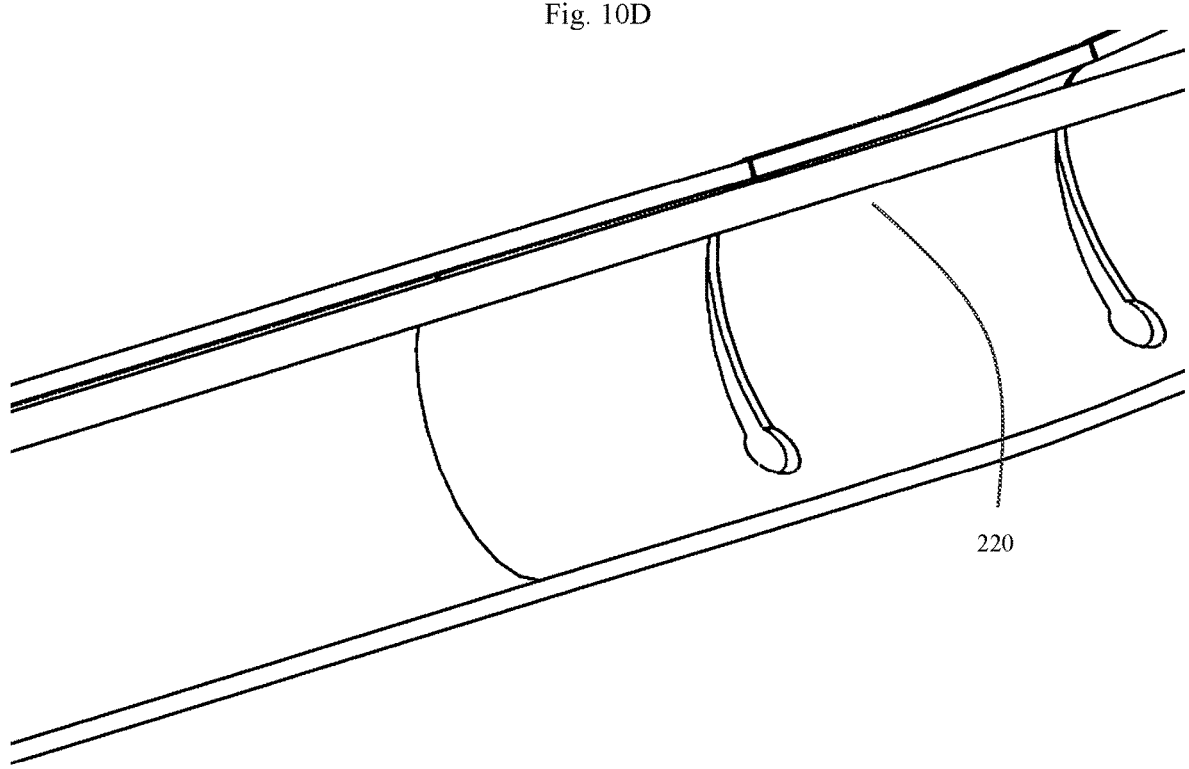
FIG. 10D shows a cross-section of a single-stage catheter. Here, the distal and proximal portions are part of the same catheter, and there is no junction or isolation transition coupler. In this embodiment, the tension cable also lacks an isolation coil.

FIG. 10D shows a cross-section of a single-stage catheter. Here, the distal and proximal portions are part of the same catheter, and there is no junction or isolation transition coupler. In this embodiment, the steering cable/tension cable (220) also lacks an isolation coil.

FIG. 11 shows how the flexible sections (106 and 108) can be tailored (e.g., custom manufactured) to fit better a patient's particular bronchi where the lesion location (e.g., target) may be a more challenging area to reach due to some pathway non-conformity.

As previously discussed, FIG. 11 also shows that any of the distal stage hollow catheter (108) and the proximal stage hollow catheter (106) may further comprise a plurality of slits (such as 108*a*, 106*a*) along at least a portion of their circumference. These slits may have positions and dimensions that are configured to facilitate catheter traversal through a series of branching body lumens of progressively smaller internal diameters. Note that in some embodiments, the proximal stage hollow catheter (106) is itself used to provide torque to the distal stage hollow catheter (108). In this embodiment, the proximal stage hollow catheter (106) is also called the torque shaft (200).

In some embodiments, the structure of a patient's particular pathway may be obtained by scanning (e.g., by using a C-arm medical imaging scanner or other type scanner to scan the patient, and to create a computed 3D model of the patient). This computed 3D model can be generated before surgery. This pathway data from the model can be used to determine the ideal trajectory of the distal stage (108). This distal stage design could be automatically generated, such as by standard computer processors or AI methods, using current patient scans (e.g., CT/MRS generated 3D models and historical data/3D scans). This data can be used to determine how to construct the distribution and flexibility of any optional flexure joints (108*a*, 106*a*) along the distal and proximal stages (106, 108) and the length of the distal and proximal stages.

Figure 12A:
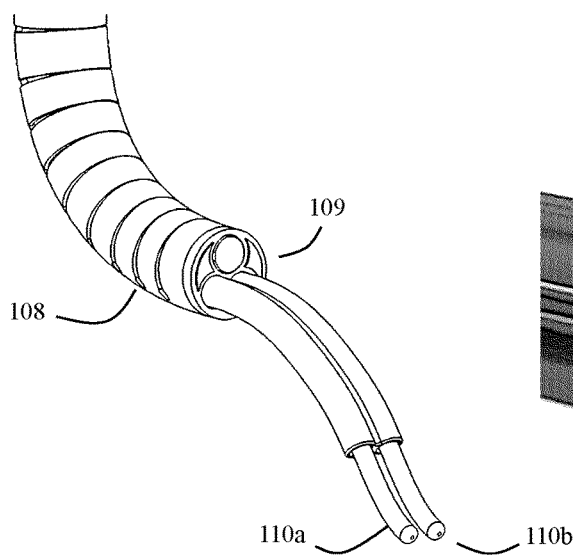
FIG. 12A and FIG. 12B show the use of optional electrodes.
Figure 12B:
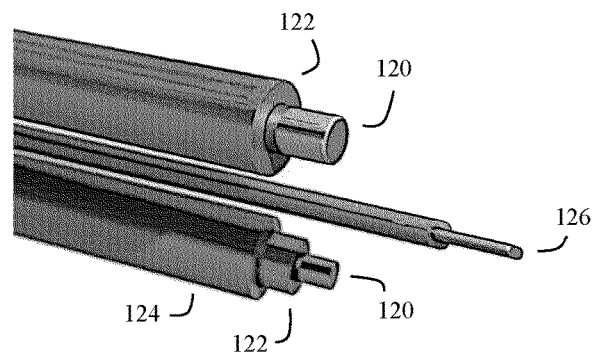

FIG. 12A and FIG. 12 B show the use of optional electrodes, such as (110*a* and 110*b*), here shown extending out of the distal plate (109). In some embodiments, bipolar (e.g., two) electrodes may be used for targeted treatment and can be used to deliver high-frequency electrical energy from a suitable source. These micro-electrodes (110*a*, 110*b*) can be isolated from one another by an insulating lumen. In some embodiments, the electrodes may be made from DFT® wire (Drawn Filled Tubing). Such DFT wire may comprise a gold core electrode (120) surrounded by nitinol (122), and often then an insulator (124). This allows for elasticity and conductivity to be optimized in small diameter wire <1 mm. Conventional wires, such as insulated copper wires, may also be used (126). In some embodiments, these wires will also have radiopacity for viewing the position of electrodes during a real-time C-Arm CT scan or other imaging process.

Thus, although some of the conduits may often comprise conduits that are tension or steering cables such as (220), at least some of the conduits may also comprise electrical conduits (such as 110*a*, 110*b*). These electrical conduits may be used to transmit any electrical power or electrical signals to any of various probes, sensors, or other electrically activated devices disposed on or passing through the distal tool plate (109).

Note further that in many embodiments, at least some of the conduits can comprise optical fibers or hollow tubes (230) configured to convey optical, electromagnetic, or radiofrequency (RF) signals or chemicals to or from devices disposed on the distal tool plate (109).

Figure 13:
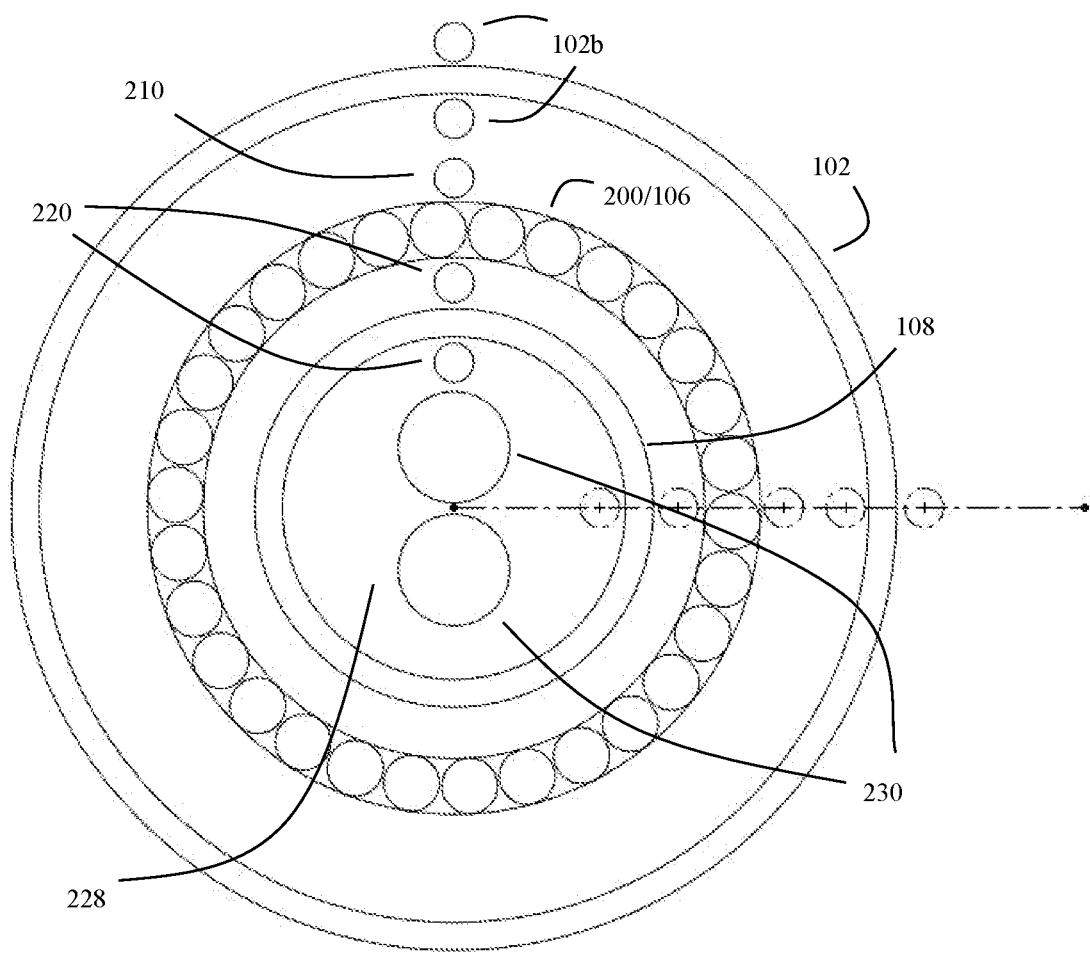
FIG. 13 shows a cross-section of the system using a 1-way Steerable Introducer Sheath, 1-way Proximal Stage, and 1-way Distal Stage with Torque Steering.

FIG. 13 shows a cross-section of the catheter system. This embodiment uses a 1-way steerable introducer sheath (102) with its own sheath steering cables (such as 102*b*).

This embodiment also comprises a proximal stage (106) or portion. In some embodiments, this proximal stage may optionally also be steerable (such as 1-way steerable) using optional proximal stage steering cables such as 210 or optionally 220 on the inside of 200/106). In some embodiments, as previously discussed, the proximal stage (106) is also a torque shaft (200).

The drawing also shows a distal stage/portion (108) configured to be 1-way steerable with its own steering cables (such as 220). The interior of the distal stage (108), and also the interior of the proximal stage (106) as well, comprises a hollow working channel (228) through which various other types of conduits, such as electrical conduits or tubes (230) and/or other items may travel.

Put alternatively, in some embodiments, at least proximal portions of the proximal stage hollow catheter are disposed within at least one hollow sheath (102). This hollow sheath (102) is configured to enable at least portions of the catheter device (e.g., 106/200, 108) to protrude or retreat inside and outside of the at least one hollow sheath (102). The extent of this extension or retraction depends on forces (manual or robotic) applied to this at least one hollow sheath (102) and at least this proximal stage hollow catheter (106). This is shown in more detail in FIG. 15, FIG. 16, and FIG. 17.

Although most examples in this disclosure use only a single steering cable/pull wire, such as (220, here sometimes shown with an exterior coil and configured as a tensioning cable), multiple steering cables may be used in some embodiments.

Figure 14:
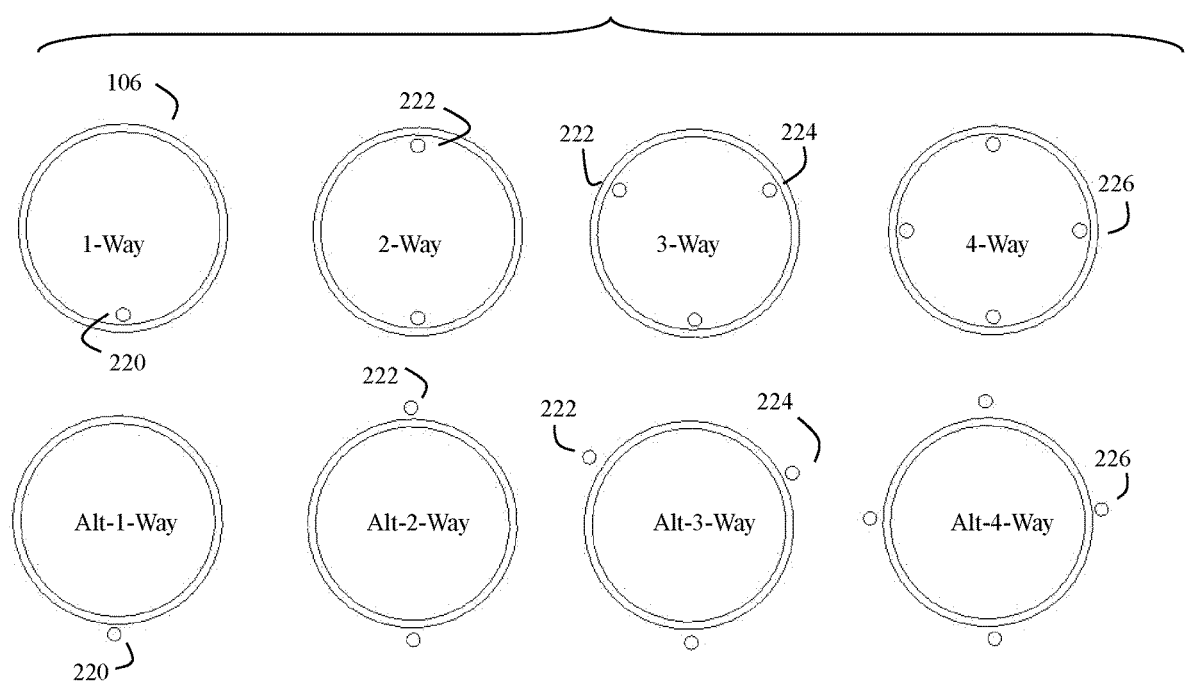
FIG. 14 shows the different pull wire orientations for each type of flexible system: 1 plane/1 direction (1-way), 1 plane/2 direction (2-way), 3 plane 3D (3-way), and 4 plane 3D (4-way).

FIG. 14 shows the different pull wire or steering cable orientations for the distal stage/portion (108) cables. Various embodiments are possible, including 1 plane/1 direction (1-way), 1 plane/2 direction (2-way), 3 plane 3D (3-way), and 4 plane 3D (4-way).

Although 4-way steering (4 steering cables) provides the highest degree of freedom of motion, there are some tradeoffs in terms of higher complexity and greater amount of interior/exterior space that is needed to accommodate larger numbers of steering cables. A smaller number of steering cables, such as 1-way steering (one-steering cable) has certain advantages because it reduces the space needed for such cables. This results in a smaller outside diameter, allowing greater access, and also allows for a catheter design with a larger working channel. This, in turn, allows for more conduits for a camera, lighting, sensors, probes, etc.

In FIG. 14, the upper row shows an interior steering cable configuration, such as shown in FIG. 10A. By contrast, the lower row (alternate) configuration is for an exterior steering cable configuration, such as shown in FIG. 5A, 5B, and FIG. 7A, 7B.

System Integration Example

As previously discussed, in some embodiments, at least the proximal portions of the proximal stage hollow catheter (106, 200) are disposed within at least one hollow sheath (102). This at least one hollow sheath is configured to enable at least portions of the catheter device to protrude or retreat inside and outside of the sheath (102), depending on forces applied to the sheath and/or the proximal stage hollow catheter (106, 200). The sheath is thus a good way to introduce the catheter into the patient's body.

Figure 15:
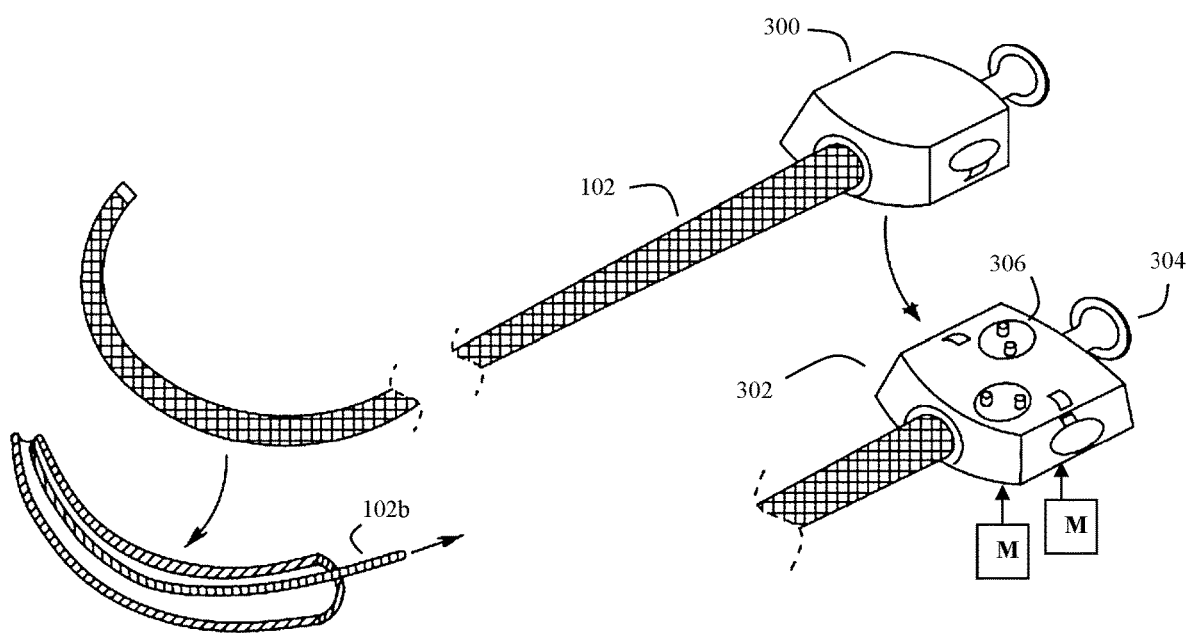
FIG. 15 shows a system example with a steerable introducer sheath control head.

FIG. 15 shows a system example of a steerable introducer sheath (102) attached to drive cartridges for a robotic system. The first cartridge or control head (300) can actuate the introducer sheath (102) to bend/flex or rotate. This hollow sheath can be used for delivering the catheter (device). In a preferred embodiment, this sheath and control head arrangement may have at least one plane of articulation (at least 1-way steering) in at least one direction. In other embodiments, the hollow sheath and control head may have up to full universal articulation (e.g., 4-way steering). In FIG. 15, the top figure shows the outside of the control head/sheath system, while the lower figure shows some of the mechanisms inside the control head/sheath system, such as a sheath articulation cable 102b and various drive wheels (306) and motors (M), often referred to as actuators (306) that can be used to manipulate the one or more sheath articulation cables.

In other embodiments, the "sheath" can comprise a mechanism that collapses but does not buckle.

FIG. 15 also shows that the articulation introducer sheath (102) can have at least one plane and one direction of articulation (here using sheath articulation cable 102b) with an axis of rotation located at the control head housing (300, 302).

Put alternatively, in some embodiments, the multi-stage catheter device can further comprise at least one control head (300). This at least one control head may comprise a hollow introducer sheath (102) and insertion funnel (304), configured to admit at least portions of the multi-stage catheter device (e.g., 106, 107, 108, 109), through the insertion funnel and hollow introducer sheath, and into a body lumen.

Figure 16:
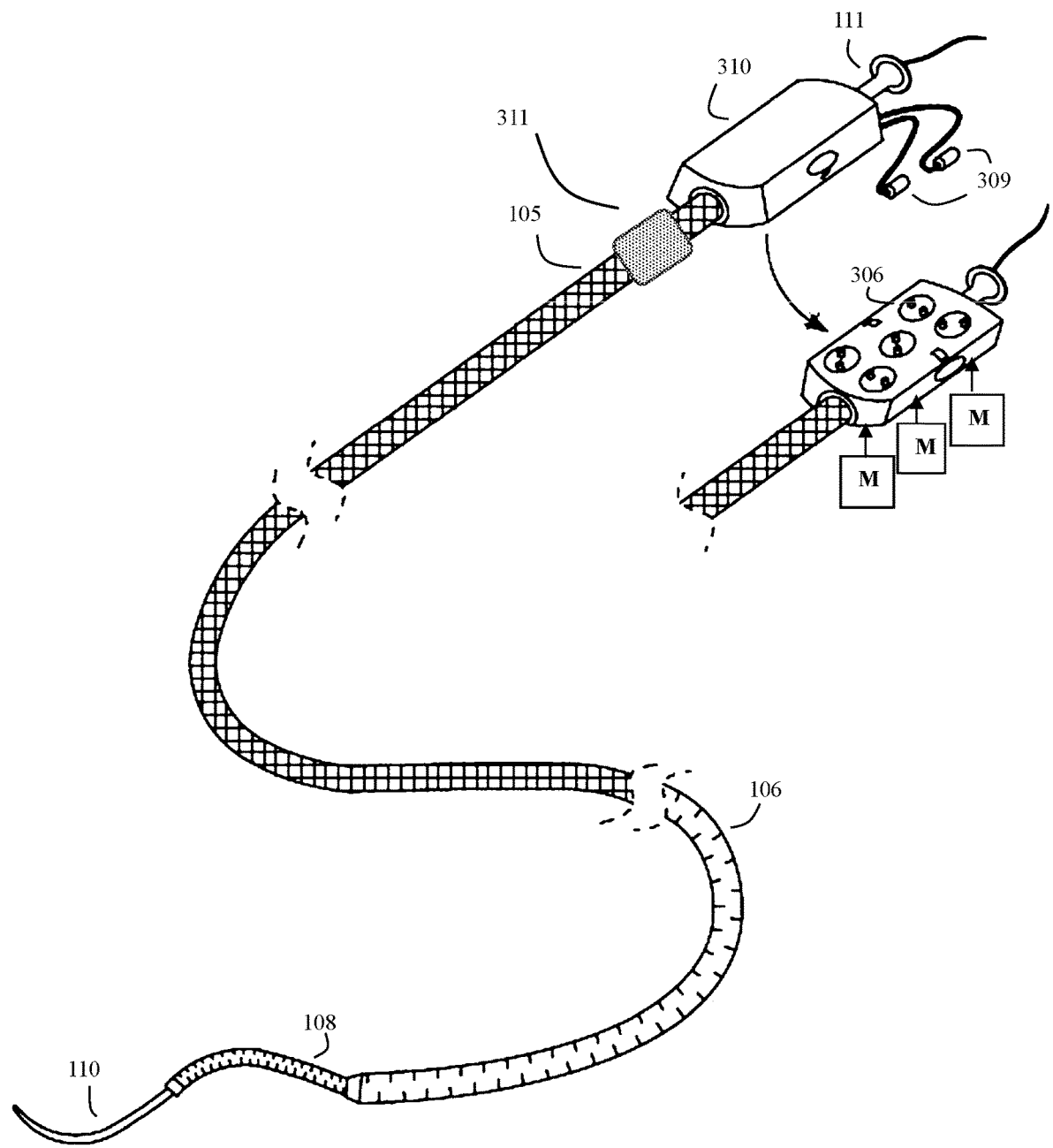
FIG. 16 shows another example of the articulating rotary robotic bronchoscope control head.

FIG. 16 shows an alternative embodiment of the catheter device control head, here designated as (310), showing other portions of the device, such as an extreme proximal portion (105) that connects to the proximal portion (106), the distal portion (108), and other portions. (Here, (105) can be viewed as an extreme proximal portion of the device that may have different flexibility than the proximal region (106), and although configured to be flexible, need not be necessarily configured to be steerable.) A conduit (111) that connects to the tool tip (110) after passing through insertion funnel (304) is also shown. This control head may also have additional drive wheels (306) and motors (M), often called actuators, which are often processor-controlled motorized actuators used to control other articulation/steering cables. Other devices shown (309) are connectors and interfaces to operate and control other conduits, such as cameras controlling cameras, lights, sensors, position indicators, electrodes, tool tips, and the like. Note that for simplicity, the introducer sheath is not shown.

Thus, in some embodiments, the at least one control head (300, 310) may be further configured with at least one computerized drive wheel (306) and motor (M), often called a motor actuator, or sometimes just an actuator. This at least one computerized motor actuator may be configured to perform any of:

Apply variable torque to the hollow torque shaft (200); and/or

Apply variable tension to any of the at least one proximal stage/portion steering cable (210) and/or at least one distal stage steering cable (220); and/or As per the FIG. 15 introducer sheath discussion, also apply variable tension to at least one sheath steering cable (102b) disposed inside the hollow introducer sheath (102).

As shown in FIG. 15 and FIG. 16, in some embodiments, the device further comprises at least one sheath steering cable (102b) connected to a distal end of the sheath. Here, this at least one sheath steering cable is disposed inside the sheath. As previously discussed, this at least one sheath steering cable (102b) may be configured to convey sheath off-axis steering force on the distal end of the sheath, causing this distal sheath and the enclosed multi-stage catheter device to move off-axis according to this sheath off-axis steering force.

To manipulate the device, the device may further comprise a sheath off-axis manual force application fixture, and/or a sheath steering cable actuator. These can be configured to further control the sheath off-axis steering force by creating and releasing tension on this at least one sheath steering cable (102b).

Although the various actuators, such as the previously discussed drive wheel (306) and motor (M) arrangements, may be part of the control head (300 or 310), in some embodiments, the actuator system may have some actuator components, such as the drive wheels (306) mounted on the control heads (300, 310), and have other components, such as the motors (M), mounted on a robotic system, such as a robotic arm.

In some embodiments, the control head (310) or an optional manual grip structure (311) attached to the sheath (102) may be used to apply manual force to the sheath if this is needed.

Note that in some embodiments, the systems shown in FIGS. 15 and 16 may be configured to be either disposable or reposable (able to be recycled a limited number of times) and will often be delivered pre-sterilized and in sterile packaging. The drive wheels (306) can be part of the disposable or reposable system, and the motors (M) that interface with the drive wheels may be configured as part of the durable medical equipment (such as part of a robotic system). After installation, the motor portions (M) may attach and detach from the drive wheels (306).

Figure 17:
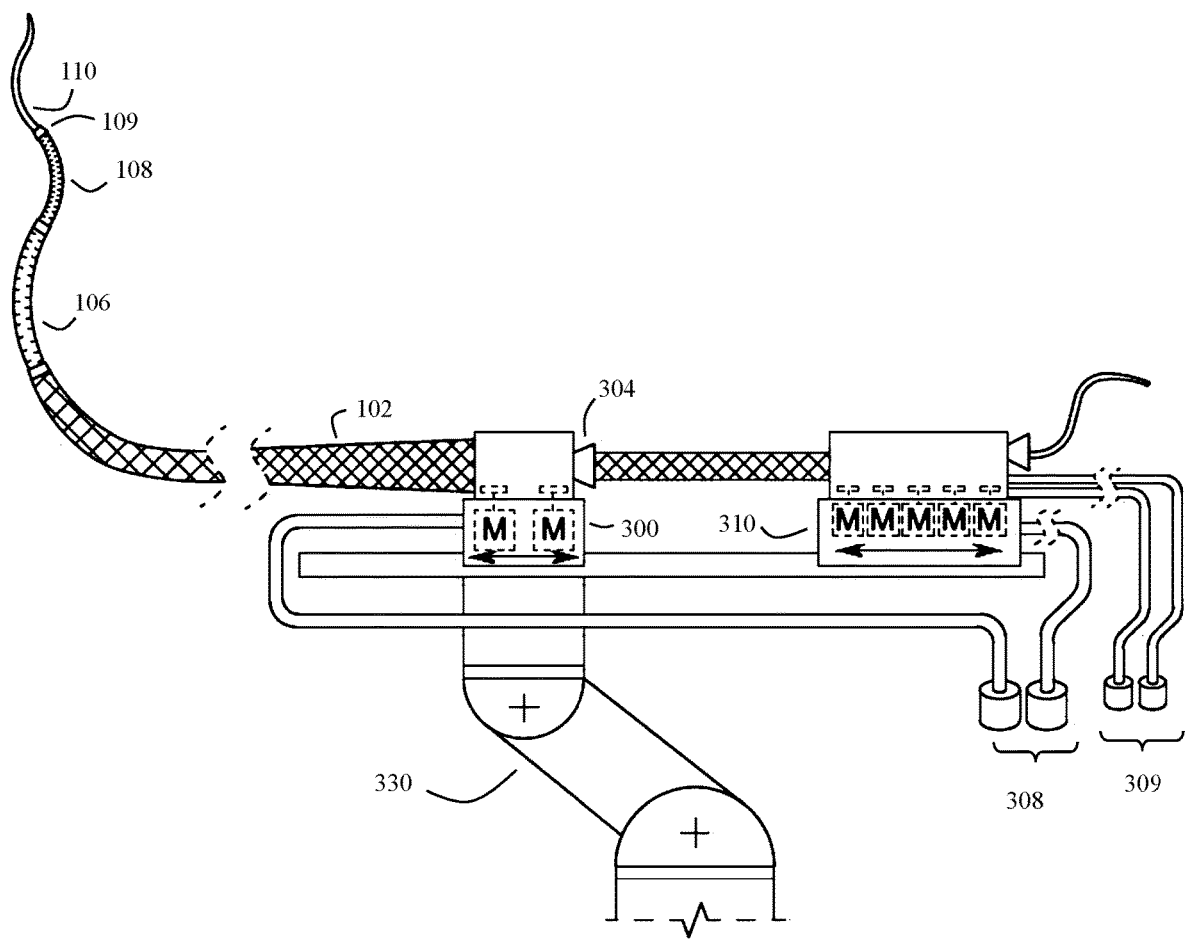
FIG. 17 shows the device implemented on a robotic system where both steerable sheath and steerable bronchoscope control heads are mounted and move independently.

FIG. 17 shows the device implemented on a robotic system where there are two control heads (300, 310), both are mounted (here on a robotic arm 330), containing blocks of motors "M" that can interface with the drive wheels (306) on the control heads. In this configuration, both control heads are configured to move independently of each other and along the same axis.

In FIG. 17, the computerized motor actuator system comprises two control heads (300, 310). These are mounted on the processor-controlled robotic arm (330). This processor-controlled robotic arm is further configured to move the catheter/bronchoscope device and control a computerized motor actuator system (such as previously discussed drive wheels 306 and motors "M) to guide at least the distal tool plate (109) of the distal end of the distal stage hollow catheter (108) to a target location. Here (308) shows the connectors and/or position encoders to control any of motors "M" and other motors to control the robotic arm's linear stages. As before, (309) shows the connectors and interfaces to operate and control other conduits, such as cameras controlling cameras, lights, sensors, position indicators, electrodes, tool tips, and the like.

Figure 18:
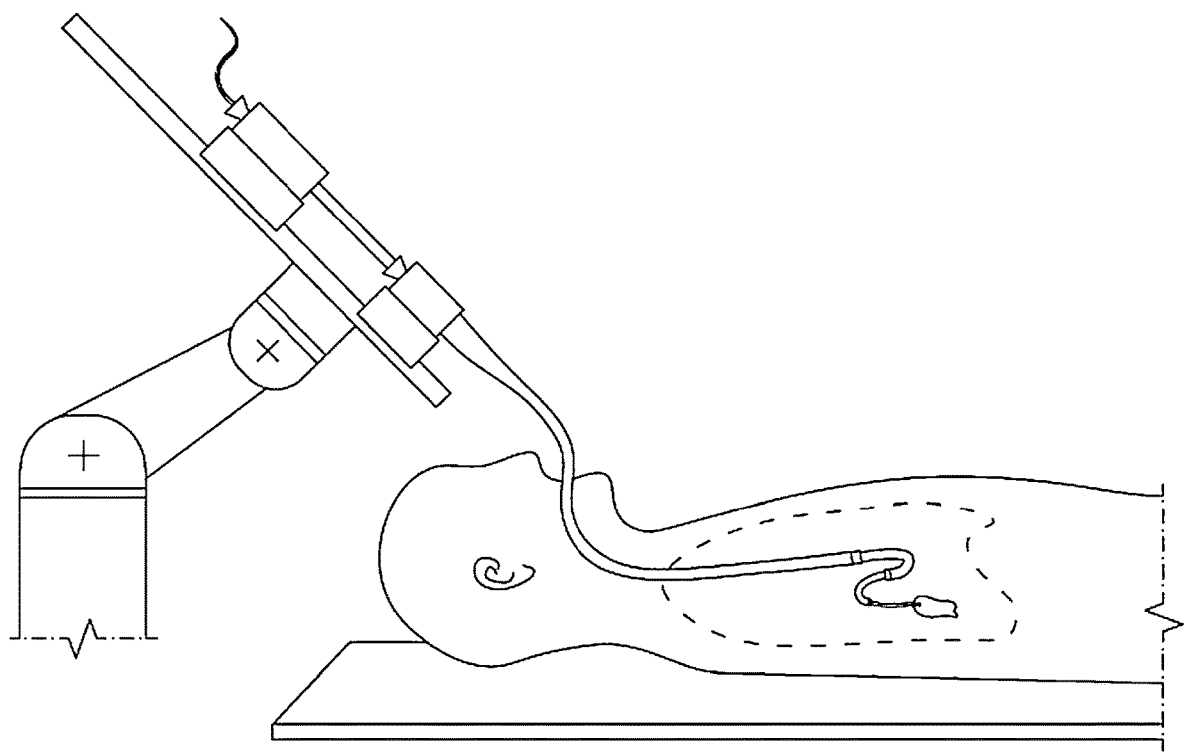
FIG. 18 shows an embodiment where the robotic system applies the catheter to a patient.

FIG. 18 shows an embodiment where the robotic system applies the catheter to a patient.

In some embodiments, at least one control head is mounted on a processor-controlled robotic arm. This processor-controlled robotic arm is configured to move the device and control at least one computerized motor actuator. These are used to guide at least the distal tool plate of the distal end of the distal stage hollow catheter to a target location (inside the patient).

The Distal Tool Head (Distal Plate)

Figure 19:
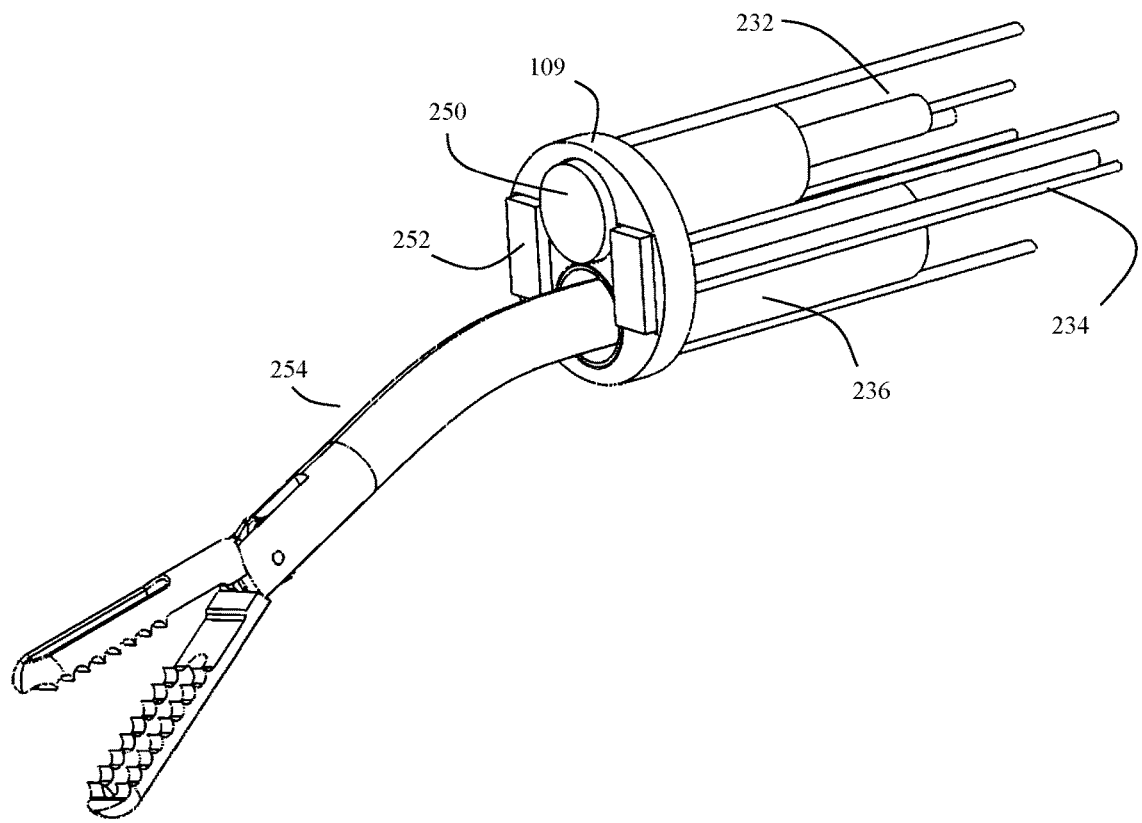
FIG. 19 shows the tool head with camera, lighting, and forceps.

FIG. 19 shows the distal tool plate (aka tool head 109) with a camera (250), lighting (252) (such as the two LED lights shown), and forceps. Here, the outer wall of the distal portion (108) is not shown (or alternatively, it has been made transparent) so that the various components and conduits (210-240) can be seen.

For example, a camera (250) may be serviced by a first electrical conduit (232), and an LED (252) may be served by a second or third electrical conduit (234). The conduits may also include hollow tubes (236), from which various devices, such as forceps (254), may be routed and controlled.

Although, in FIG. 19, the distal tool plate has an opening that is not as large as the inner diameter of the distal stage hollow catheter, this need not be limiting. In some embodiments, the distal tool plate (109) may be configured with an opening with a distal tool plate opening diameter as large as the inner diameter of the distal stage hollow catheter.

Put alternatively, the distal stage (distal portion 108) often has a tool head (109) at its distal end, alternatively called the distal tool plate. Although the examples so far have mostly just shown electrodes (110) as one type of tool, many alternative tools and configurations are also possible. As shown in FIG. 19, this tool head (109) may be alternatively, or additionally, fitted with other devices such as a camera, light source, and a tube or opening for delivering tools, e.g. forceps, brushes, biopsy needles, electrodes, drug delivery needles, and the like.

As previously discussed, although the distal tool plate will usually obscure at least some part of the distal opening of the distal stage hollow catheter (108), alternative embodiments are possible. In some embodiments, the distal tool plate (109) may be configured with a distal tool plate opening diameter that is as large as the inner diameter of the distal stage hollow catheter (108). Note that this large-opening distal tool plate will still be configured to attach to the steering cables (220 . . . 226). See FIG. 9 as an example. Alternatively, the cable can also be attached just proximal of the plate to the inside or outside of 108 by adhering, snap fit, soldering or welding.

In some embodiments, at least some of the conduits may comprise electrical conduits (234) configured to transmit electrical power or electrical signals to probes, sensors, or other electrically activated devices disposed on or passing through the distal tool plate.

Alternatively, or additionally, in some embodiments, at least some of the conduits (234) may comprise optical fibers or hollow tubes configured to convey optical, electromagnetic, or radiofrequency (RF) signals or chemicals to or from devices disposed on the distal tool plate.

Figure 20A:
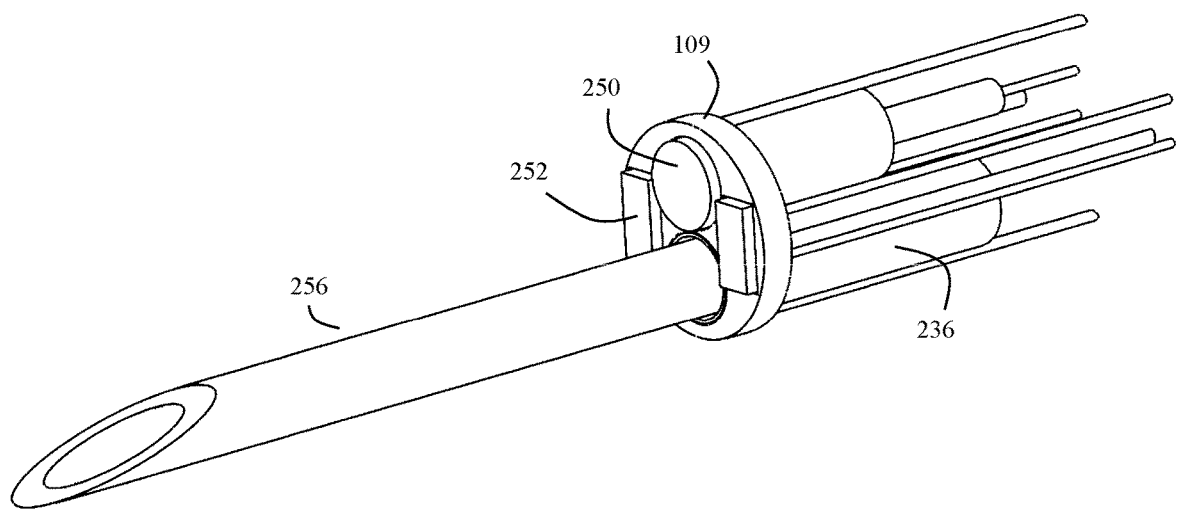
FIG. 20A shows the tool head with a biopsy needle.

FIG. 20A shows the tool head (109) with a biopsy needle (256).

As shown in FIG. 20A, in some embodiments, at least some of the conduits (such as 236) and the distal tool plate (109) may be configured to obtain tissue biopsies from a target tissue, or to administer therapy to a target tissue.

Figure 20B:
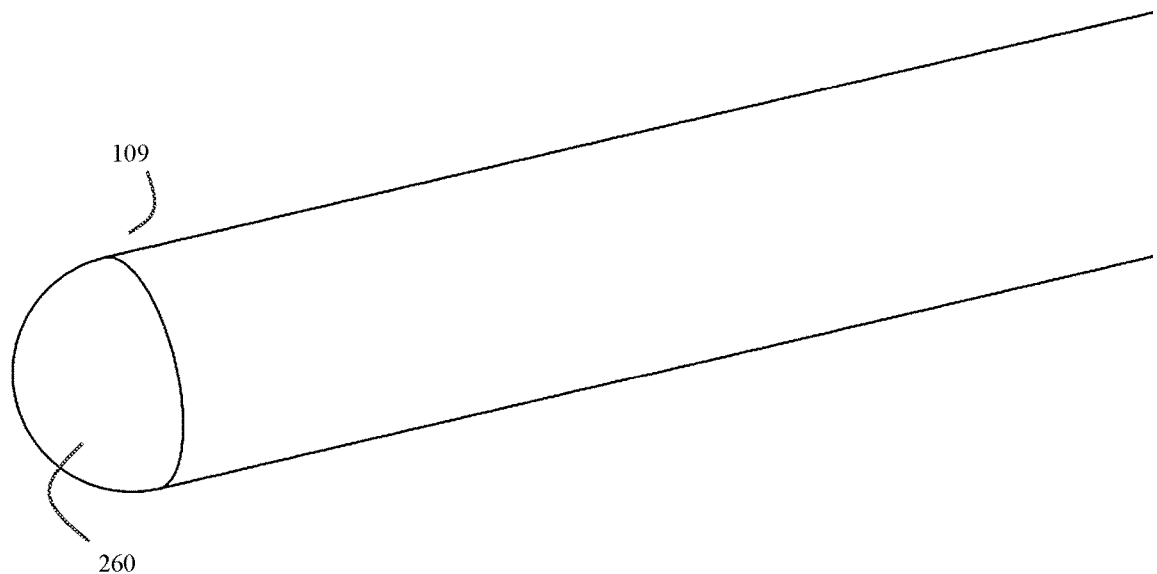
FIG. 20B shows a tool head with a closed tip.

FIG. 20B shows a tool head with a closed tip (260).

Figure 20C:
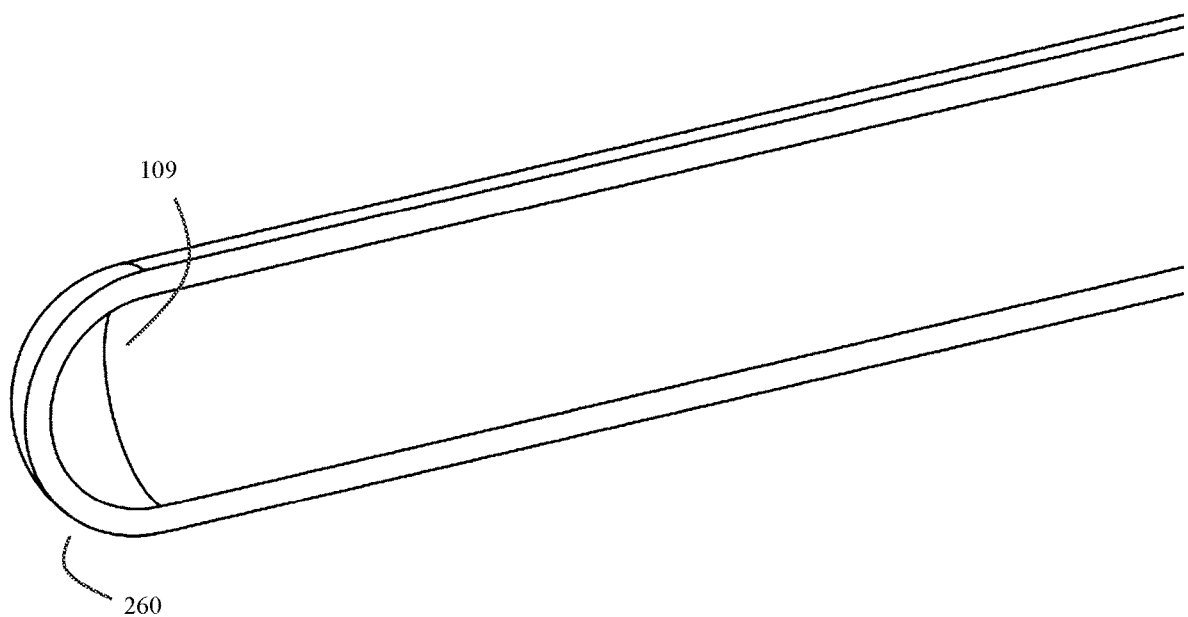
FIG. 20C shows a cross-section of the tool head with a closed tip previously shown in FIG. 20B.

FIG. 20C shows a cross-section of the tool head (109) with a closed tip (260) previously shown in FIG. 20B. Various versions of the closed tip are possible, including the round tip (shown), a pointed tip, and a tip with a softened edge. Such tips can be made from conductive or nonconductive materials and used for various purposes, such as electrophysiological monitoring and cardioversion shock therapy. The tip or near the tip in some cases may have very small holes for delivering fluid such as saline or a drug therapy.

Thus, in some embodiments, the most distal tip of the catheter's distal stage/portion need not be hollow. Indeed, depending on the configuration, up to the entire distal stage/portion may be filled with either the same material as the catheter wall itself or other material as desired.

Figure 21:
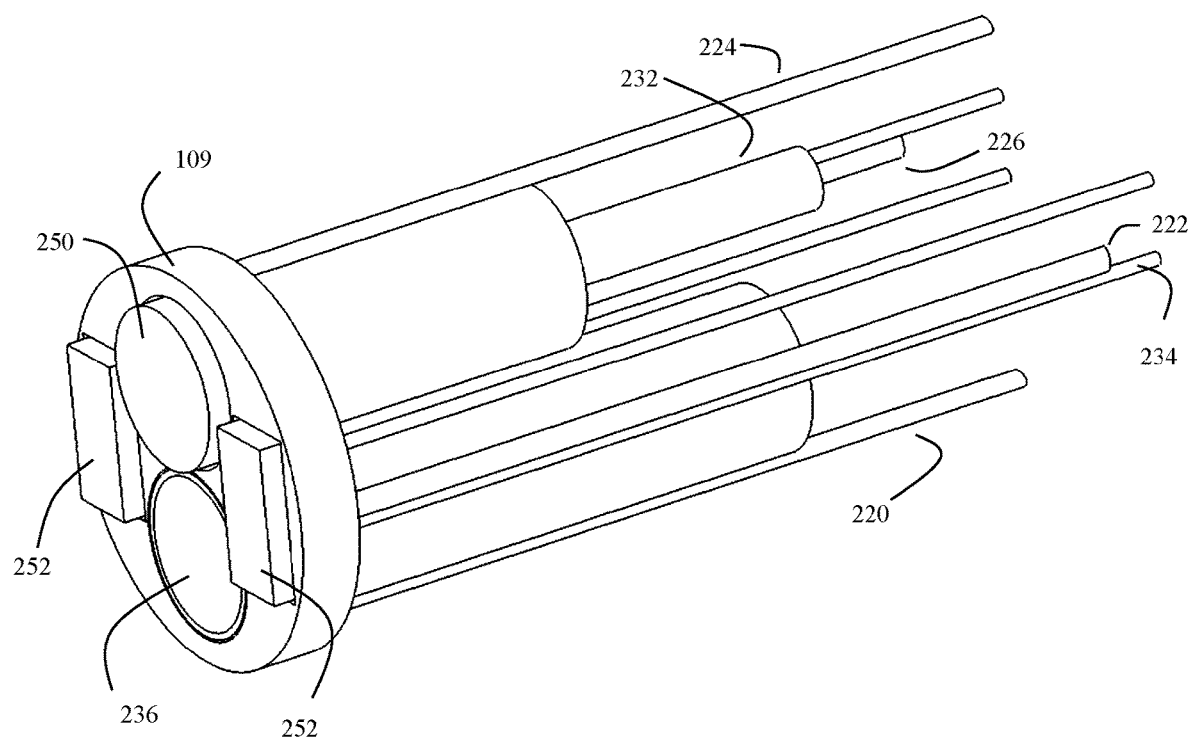
FIG. 21 shows some components that may be integrated into the tool head's tool plate.

FIG. 21 shows another view of some of the components and conduits that may be integrated into the tool head's tool plate (109). Here, this includes a camera (250), a working channel, which can also be viewed as a hollow tube conduit (236) for delivering tools, and two LED lights (252). Coming off the tool plate (109) are the four previously discussed pull wires, conduits, or cables (220, 222, 224, and 226) for a 4-way distal stage articulation (e.g., X, Y, and Z axis movement, or 3D articulation). The conduit leads (232), (234) for the camera and LEDs are also shown. The camera (250) can be any type of small video camera, including a CMOS, CCD, or fiberscope. The LEDs (252) can be replaced by fiber optics lighting as desired, in which case some of the conduits (such as 234) may be optical fibers.

It will often be useful to use various types of location tracking or imaging devices to determine the location of the device, in particular, the tool plate (109) and/or associated tools while in use. Thus, in some embodiments, any of the distal tool plate (109) or portions of the conduits may comprise any of optical or radiofrequency detectors or emitters or radio-opaque materials configured to enable a location of the distal tool plate or portions of the conduits to be determined.

As previously discussed, often the optical detector (250) may be a video camera, and the emitter (such as 252) may be configured to emit light for this video camera.

Additional Distal Plate Discussion:

As previously discussed, the distal plate, also called the distal tool plate (109), is a main structural component, often disk-shaped, that is positioned on the distal end of the distal segment or portion (108). The distal tool plate holds various conduits that send electrical or chemical signals to and from the distal end of the device and the operator or computer at the proximal end of the device. The distal tool plate can also provide access for tools to reach the area of treatment.

As previously discussed, FIG. 21 shows an embodiment of the tool plate (109) that locates and mounts a video camera (250), two LEDs to provide light (252), and a hollow tube conduit (236) that can be used as a tool port.

Alternate embodiments of the tool plate (109) may have two hollow tube conduits (236) providing two tool ports, a camera (250), and two LEDs (252).

In some embodiments, the tool plate (109) may have a tool port (238) providing another type of conduit that can provide a guide feature to introduce bipolar electrodes (such as (110*a* and 110*b*), or other tools, plus a camera (250) and LEDs (252).

Methods of Biopsy, and Delivering Therapy at the Tool Head

In some embodiments, a needle may be used to retrieve a biopsy from a lesion location using the catheter device.

In some embodiments, the system may be used for monopolar therapy methods (here defined as providing therapy using only one probe), such as using the device to inject a drug into a cancerous tumor. Alternatively, other monopolar therapy methods may be used, such as by treating a cancerous tumor with radiofrequency (RF) mono-polar energy from a single electrode to either treat the tumor directly or activate a drug that, in turn, attacks the tumor.

Alternatively, the bi-polar therapy method, here defined as providing therapy using two probes) may be used. Here a drug can be injected into a cancerous tumor using a first probe or needle.

There is a return needle that is also injected into the tumor, which may either be used to deliver a second drug, more of the first drug, or return excess drug from the tumor.

As another example of a bi-polar therapy method, a cancerous tumor can be treated with RF (radiofrequency) energy between two electrodes to either treat the tumor directly or activate a drug to, in turn, attack the tumor. Alternatively, bipolar RF energy may be used to treat a tumor by activating a payload comprising a therapeutic. In this case, two (or more) electrode needles are spread out into the tumor.

As yet another example, a tumor can be injected with a single needle, and this same needle can act as a first electrode to deliver RF energy. Here, the head plate (109) or the body of the catheter (108) can act as a second electrode. Thus, with this arrangement, an electrode can be exposed at the front of the catheter, and bi-polar RF energy can return through the body of the catheter.

Drive Methods, Crawling

In some embodiments, the catheter can be made to crawl through tissue with an undulating wave which can be set up between the distal (108) and proximal (106) stages. This motion, along with the rotation of the distal stage (induced by hollow shaft 200), can produce a crawling or serpentine-like movement. With the spinning distal stage, while also flexing, the stage can drive further into a body lumen (such as a vessel or bronchi) towards the desired target.

In some embodiments, the device motion may be controlled by one or more processors, which drive the actuators/motors (often in a control head) to create a type of wave between the distal (108) and proximal stages (106).

Further Discussion

Any of the following instruments may pass through the device to a distal end effector at the device's distal end: cameras and lighting; needle biopsy devices; brush biopsy devices; forceps biopsy devices; debrider biopsy devices; RF coagulation/cutting devices (monopolar, bipolar); probes; sealing devices; and the like. Similarly, the joints and devices described herein may be used or adapted for use in any suitable medical or surgical procedure, including but not limited to: debrider tumor resection, shears tumor resection, delivery of biologics and medications, neural tumor resection, polyp resection or biopsy, breast biopsy, lung biopsy, minimal portal access heart bypass, endoscopic submucosal dissection, transurethral procedures (TURP, bladder tumors) prostatectomy, hysterectomy, stem cell delivery, delivery of arthroscopic tools, knees and hips, and transnasal procedures (frontal sinus tissue removal, functional endoscopic sinus surgery, etc.). These are only examples, however, and any other end effectors and procedures may be used in various alternative embodiments.

Further Discussion of Various Systems and Methods for Driving the Catheter

As will be discussed, in some embodiments, the invention may be a device, system, or method of actuator-assisted or robotically driving a catheter device for traversing internal body passages. As previously discussed, this catheter device will typically have at least one stage, and may, for example, comprise a distal-stage hollow catheter (108) and a different proximal-stage hollow catheter (106).

In this configuration, one end of the distal stage hollow catheter may be affixed to the end of the different proximal stage hollow catheter by an optional isolation transition coupler (107a, 107a1, 107a2 or junction (107j).

This optional isolation transition coupler, if present, is typically configured to traverse an internal body passage. It typically comprises a transition housing (107a) that may optionally include at least one distal coil stop (107b) for an optional isolation coil. This coupler may be configured to enable one end of the distal stage hollow catheter to attach to the end of the different proximal stage hollow catheter.

The catheter device will further comprise a hollow torque shaft (200), which in some embodiments forms the proximal stage/portion hollow catheter (106). The hollow torque shaft may be attached to the optional isolation transition coupler (107a) or junction (107j). This hollow torque shaft is configured to convey torque to the coupler or junction, and the distal stage/portion hollow catheter (108).

The catheter device will further comprise at least one distal stage/portion steering cable (220). This cable is connected by and through the optional isolation transition coupler (107a). This at least one distal stage steering cable can be disposed either inside or outside the proximal stage hollow catheter (106) or hollow torque shaft (200). At least one distal stage steering cable (220) is configured to convey the distal stage steering force to the tool plate (109), causing the tool plate and the distal stage hollow catheter (108) to move (e.g., flex) according to the distal stage steering force.

The hollow torque shaft (200), distal stage/portion hollow catheter (108), and optional isolation transition coupler (107a) typically further comprise a working channel (See FIG. 13, 228) configured to convey a plurality of conduits through the proximal stage hollow catheter and the distal stage hollow catheter to at least a distal tool plate (109) mounted on a distal end of the distal stage hollow catheter (108).

In a preferred embodiment, at least some of the conduits comprise at least one distal tool plate steering cable (220) that is connected to the distal tool plate (109) on the distal end of the distal stage/portion hollow catheter. This at least one distal stage steering cable (220) is configured to convey distal stage steering force on the distal tool plate (109). This causes the distal tool plate and the distal stage catheter to further move (e.g. flex or unflex) according to the distal stage steering force.

In terms of a device, system, or method of driving the above catheter, expressing the invention in methods format, the invention will typically comprise flexing and unflexing the end of the distal stage/portion hollow catheter. This can be done by using at least one distal stage tensioning actuator (for example, any of 350/1, 350a/1), to create and release tension on at least one of the distal stage steering cables (220). This is typically done while also rotating this least one distal stage steering cable in a 1:1 ratio with any rotation of the torque shaft (200), which is coupled by the optional isolation transition coupler (107a) or junction (107j), or directly (for a one stage catheter) to the connected distal stage hollow catheter (108).

Driving Mechanisms:

In some embodiments, the catheter device may further comprise at least one distal stage/portion tensioning actuator (350/1) configured to flex and unflex the end of the distal stage hollow catheter by creating and releasing tension on at least one of the distal stage steering cables (220), A key aspect of this embodiment is that this at least one distal stage/portion tensioning actuator is further configured to rotate this at least one distal stage steering cable (220) in a 1:1 ratio with any rotation of the distal stage/portion hollow catheter (108). Since, in a preferred embodiment, the distal stage/portion catheter (108) is rotated by the proximal stage/portion catheter (106) and torque shaft (200), this means that the distal stage steering cable (220) is rotated in a 1:1: ratio with any rotation of the torque shaft (200). Thus, suitable mechanisms must provide this synchronized steering cable actuation (220) and catheter rotation.

Figure 22A:
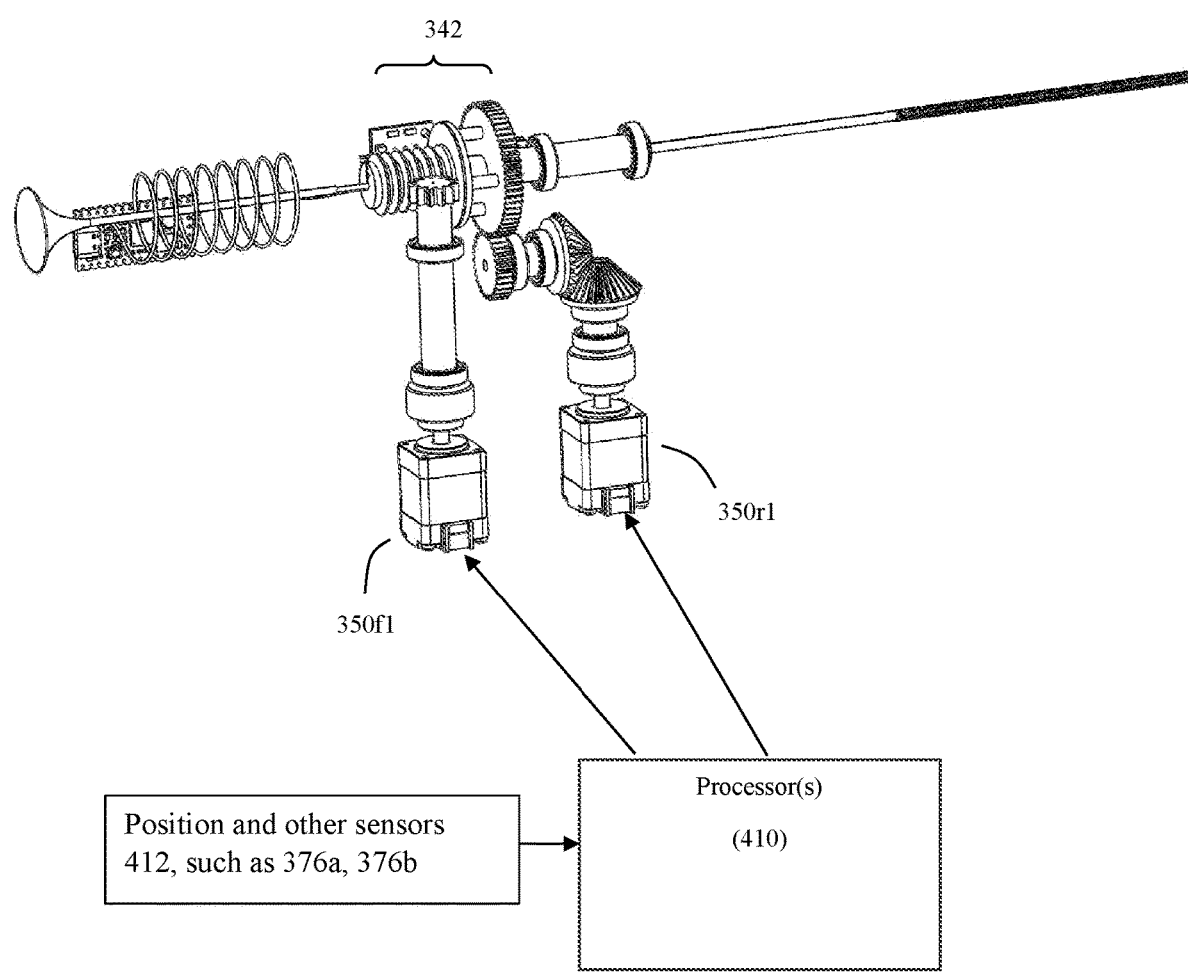
FIG. 22A shows another example of how the catheter device can be driven.

FIG. 22A shows an example of how the catheter device can be synchronously driven. In this embodiment, the robotic system uses both rotary torque mechanisms and linear actuation mechanisms. These two types of mechanisms (342) are coupled together to produce both rotary motion and linear motion at the same time. In some embodiments, multiple rotary torque mechanisms and linear actuation mechanisms (e.g., multiple iterations of 342) may be ganged up together to operate multiple tensioning cables and/or create multiple rotary degrees of freedom simultaneously.

In some embodiments, the invention may move the optional isolation transition coupler (107*a*) or junction (107*j*) by using a different proximal stage tensioning actuator to create and release tension on at least one of the at least one optional set of proximal stage steering cables (210). Again, this is done while also rotating this optional set of proximal stage steering cables (210) in a 1:1 ratio with any rotation of the proximal stage/portion hollow catheter and the distal stage/portion hollow catheter, often by using another gang of linear actuators and rotary drivers similar to 342.

Figure 22B:
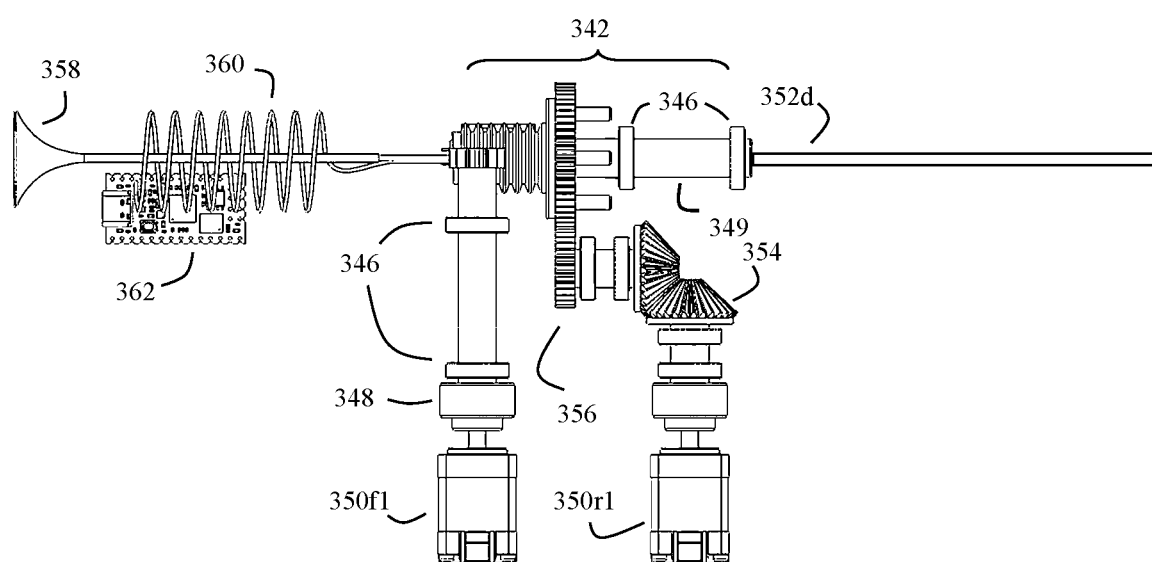
FIG. 22B shows further details showing how the FIG. 22A robotic drive system can operate

FIG. 22B shows further details showing how this robotic drive system (342) can operate. Each drive section may further comprise bearings (346), distal and/or proximal drive body shafts (349, 347), optional motor drive couplers (348), and motors/actuators. In some embodiments, these motors/actuators are electromagnetic motors/actuators, often controlled by suitable processors and sensors.

In the single gang option shown, the rotation of the proximal portion of the catheter torque shaft (108/200) can be controlled by a rotary shaft actuator (350*r*1), while the movement of the distal stage steering cable (220) (or tensioning cable) can be controlled by the distal stage flexing actuator (350*f*1). Because, in this embodiment, the distal stage (108) is firmly coupled to the proximal stage/rotary shaft (106/200) by the optional isolation transition coupler (107*a*) or junction (107*j*), rotation of both the distal stage/portion and the proximal stage/portion is controlled by the same rotary shaft actuator (350*r*1).

Thus, the motors/actuators include "tensioning motors/actuators" (350*f*1) and "rotate motors/actuators" (350*r*1). Other components can include torque shafts (200), potentially the outside of the proximal portion of the catheter (106), miter gears (354), and other types of gear arrangements (356). Additional components may include an insertion funnel or lure lock device (358), optional electrical wire coils for camera or therapy devices (360), and other electronic components such as sensors and drive circuitry (362).

As will be discussed shortly, the "tensioning motors/actuators" (350*f*1) are generally configured (often with suitable gear assemblies) to "flex" or "bend" or "steer" at least the distal stage/portion of the catheter, usually by controlling tension on a suitable steering cable such as (220). By contrast, the "rotate motors/actuators (350*r*1) are generally configured (again with suitable gear assemblies) to rotate that particular steering cable, usually in conjunction with other rotations of the catheter device (e.g., torque shaft rotations 200), to prevent the various cables from tangling with each other as portions of the catheter device rotate (as required to traverse various body passages).

Definition: Those mechanisms convert the force between various processor-controlled electromagnetic actuators into a desired mechanical movement are generally defined as "contacting mechanisms." Here, a "gear assembly" can be a specific type of contacting mechanism, but other contacting mechanisms that don't use gears may also be used.

In some embodiments, the invention may also comprise using at least one distal stage tensioning actuator (350*f*1) and at least one contacting mechanism. These actuators often comprise at least one processor-controlled (410) electromagnetic actuator. To assist in precise movement, often at least a motion or position sensor (e.g. 412, 376*a*, 376*b*) may be analyzed by this least one processor during this process to control one or more actuators. In some embodiments, the actuator(s) may have built-in motion or position-sensing ability, in which case the sensor(s) may further comprise such built-in sensors.

As shown in more detail in FIGS. 22A and 22B, the Axis of Rotation (352*d*) for all catheter stages is defined at the motor drive axis where the mechanical drive system rotates at least one or more catheter stages.

Put alternatively, in some embodiments; the device may comprise at least one distal stage tensioning actuator. This distal stage tensioning actuator may comprise at least one contacting mechanism (such as a gear assembly), at least one electromagnetic actuator (350*f*1, 350*f*2), and at least one processor-(410) configured to control at least one electromagnetic actuator. Additionally, in a preferred embodiment, the device comprises at least one motion or position sensor such as (412, 376*a*, 376*b*). Here, the at least one processor (410) is further configured to use input from the at least one motion or position sensor to control this at least one electromagnetic actuator.

In some embodiments, as previously discussed, the at least one contacting mechanism comprises at least one gear assembly (e.g., any of 354, 364, 366, 368, 370, 375, as shown in FIG. 22B). Further, at least portions of this gear assembly may be configured in a disposable or reposable cartridge that can be reversibly coupled and decoupled from the at least one electromagnetic actuator such as 350*f*1, 350*f*2.

Figure 31A:
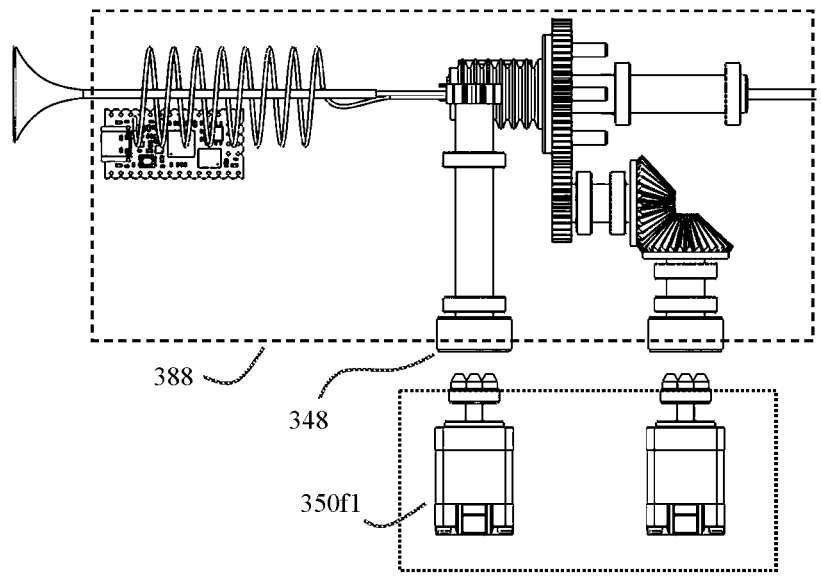
FIG. 31A shows how a disposable housing or cartridge may contain the proximal drive side (or gear train) of the multi-stage catheter driving assembly.

The disposable and reposable aspects are discussed in more detail in FIG. 31A.

FIG. 22B shows more details of how the mechanical drive system can operate to rotate various sections of the catheter device.

As previously discussed, in a typical embodiment, at least some, and often all, of the various actuators (such as 350*f*1, 350*r*1) will be electromechanical actuators. These will typically be driven under processor control by one or more processors (usually one or more microprocessors (410). The microprocessors, in turn, will usually receive input from one or more sensors (412), such as the various sensors (376*a*, 376*b*), which will be discussed shortly.

Although electromagnetic actuators are often given as a specific example, other actuators, such as electro-active nitinol and polymers, air-driven actuators (pneumatic actuators), or fluid drive actuators, may be used.

Figure 23:
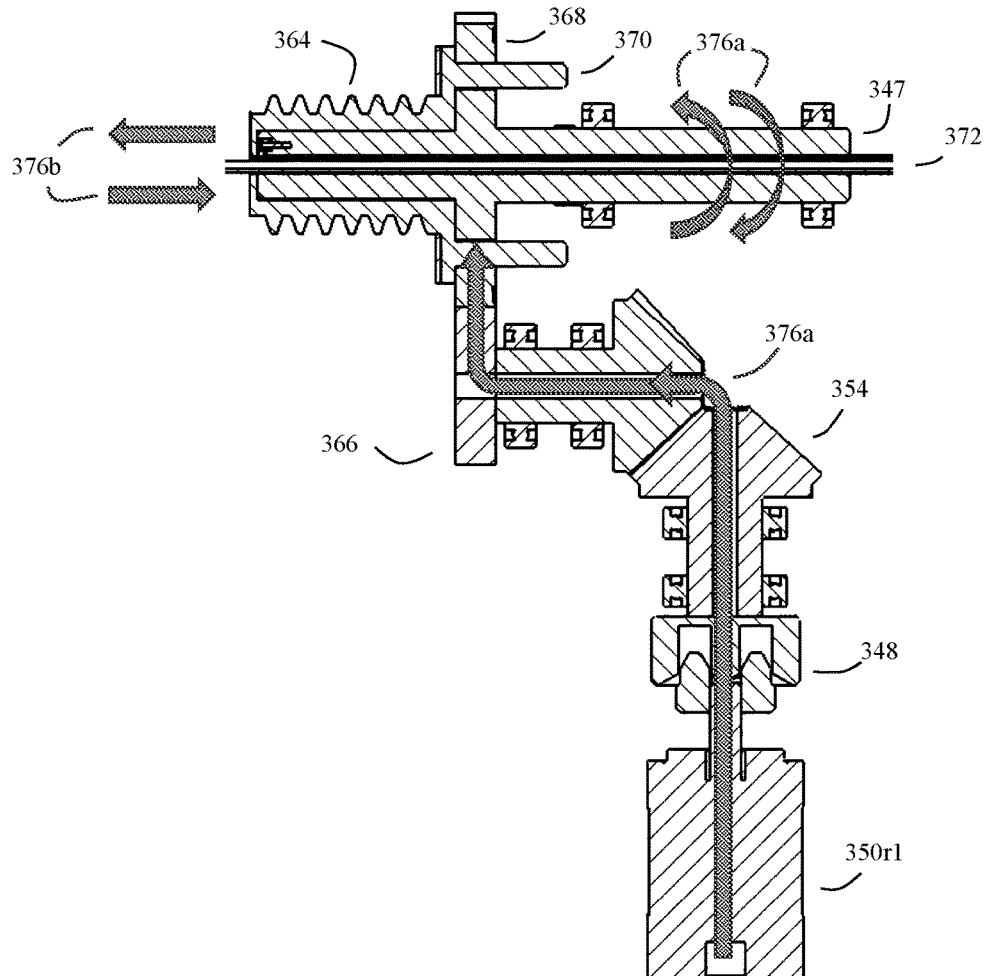
FIG. 23 shows a cross-section of the device previously shown in FIGS. 22A and 22B.
Figure 24:
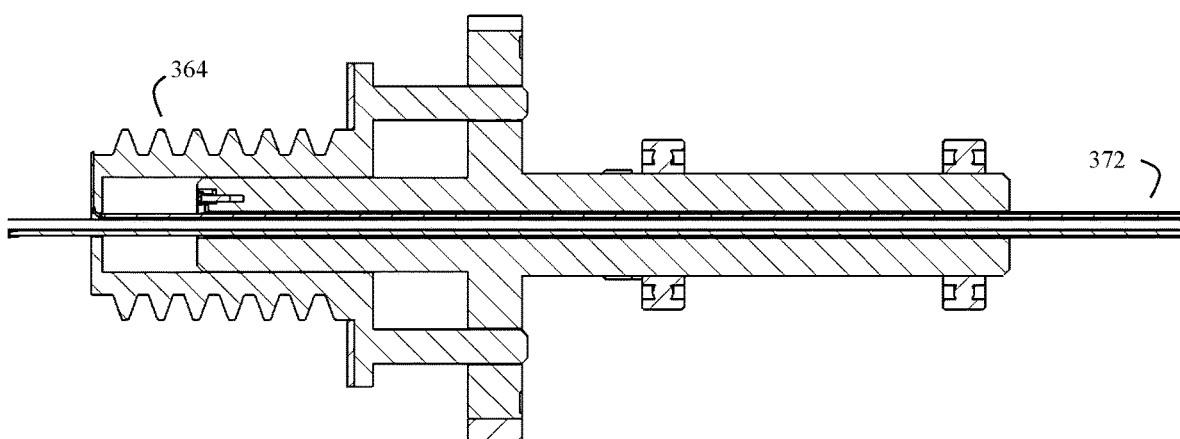
FIG. 24 shows a close-up cross-section of the drive rack, transfer gear, rotary drive gear and sliding drive pins portions of the device previously shown in FIGS. 22A, 22B, and 23.

FIG. 23 and FIG. 24 show how the Distal Linear Circular Gear Rack (364) slides along the Drive Body Shaft. These figures also show how the Distal Circular Gear Rack is driven by the Rotary Drive Gear, which is solidly connected to the Drive Body Shaft, which in turn is adhered to the Proximal Torque Shaft of the catheters. In this embodiment, the Linear Circular Gear Rack slides along the Drive Body Shaft, while it is coupled to drive pins sliding through the Rotary Drive Gear. This coupling keeps the steering cable (220) from becoming twisted while being actuated by the Linear Circular Gear Rack while rotating 1:1 with the Drive Body Shaft (e.g. torque shaft 200). There are many other ways to slidably mate the Linear Circular Gear Rack to the Drive Body Shaft for transferring torque. These include as keyway devices, flats (single, double . . . hex, etc.), pins, splines, or other mechanisms. The slidable mate (e.g., pins 370 or another mechanism) allows transverse movement along the rotating member or catheter axis while constraining movement radially from the rotating member or catheter axis.

FIG. 23 shows a cross-section of the device previously shown in FIG. 22A and FIG. 22B. This shows a linear, circular drive rack (364), transfer gear (366), rotary drive gear (368), optional sliding drive pins (370) and a suitable steering cable (372), such as the distal stage steering cable (220) previously discussed. Note that, in some embodiments, there may be a plurality of versions of this device, one (342) configured to operate the distal portion of the catheter, and others configured to operate additional steering cables or sheaths.

The large arrows show the various directions of motion of the respective components during operation. As can be seen, the device both rotates (376*a*) about its axis (along 372), and also can be commanded to have an axial in and out motion as well (376*b*). The power transmission path from the actuator (350*r*1), through various optional intermediary gears such as (354) and (366), to the rotary drive gear (368) is shown as (376*a*).

Again, the "in and out" motion (376*b*) is used to apply or release tension to a given steering cable (such as 220) that is used to flex or unflex or "steer" at least the distal portion of the catheter. The rotary motion is designed to prevent the steering cables from getting tangled while, for example, various portions of the catheter are rotated to traverse various body lumens, such as by using the previously discussed hollow torque shaft (200).

Put alternatively, in some embodiments, the rotary drive gear (368) rotates the drive body shaft (347), which is connected to the outer proximal tube body and torque shaft (e.g. 347 to 106/200).

In some embodiments, the distal linear, circular gear racks (364) (distal 342) rotate while also coupling their rotation to the sliding drive pins (370). These gear racks are driven to rotate 1:1 by their respective rotary drive gears (368). While any given linear circular gear rack (364) (distal 342) is rotating, it can be actuated for "in and out motion" or "tensioning motion" (376*b*) along the axial direction (372) by a linear circular pinion gear, (see FIG. 25, 374), which is allowed to slide in the grooves cut in (364) while (364) is rotating and be driving by sliding drive pins (370) on the appropriate drive body shaft.

In this embodiment, rotary motion is directed from the motor/actuator (350*r*1) through a contacting mechanism comprising a motor coupler (348) to miter gears (354), then to the transfer gear (366), and finally to the rotary drive gear (368). In some embodiments, one or more contacting gears such as these may also be termed a "gear assembly."

Note that in some embodiments, the proximal outer tube body (106) may be glued, mounted, or otherwise adhered to its respective drive body shaft (347). In this embodiment, the proximal drive body shaft (347) may be used to directly turn the proximal outer tube body (106) and torque shaft (200). This controls the rotation of the isolation translation coupler (107*a*) and is conducted directly to the distal catheter portion (108).

Steering cables (220) can cause the distal portion of the catheter (108) to flex or curve in any rotational position.

FIG. 24 shows a close-up cross-section of the drive rack (364), transfer gear (366), rotary drive gear (368), and sliding drive pins (370) portions of the device previously shown in FIGS. 22A and 22B. This shows more details of how this device accomplishes both rotation and in-and-out steering cable sliding motion. Here the linear circular gear rack (or drive rack) (364) is shown fully extended. The drive rack (364) has pulled the steering cable (220, 210) to a fully flexed state in this configuration.

Figure 25:
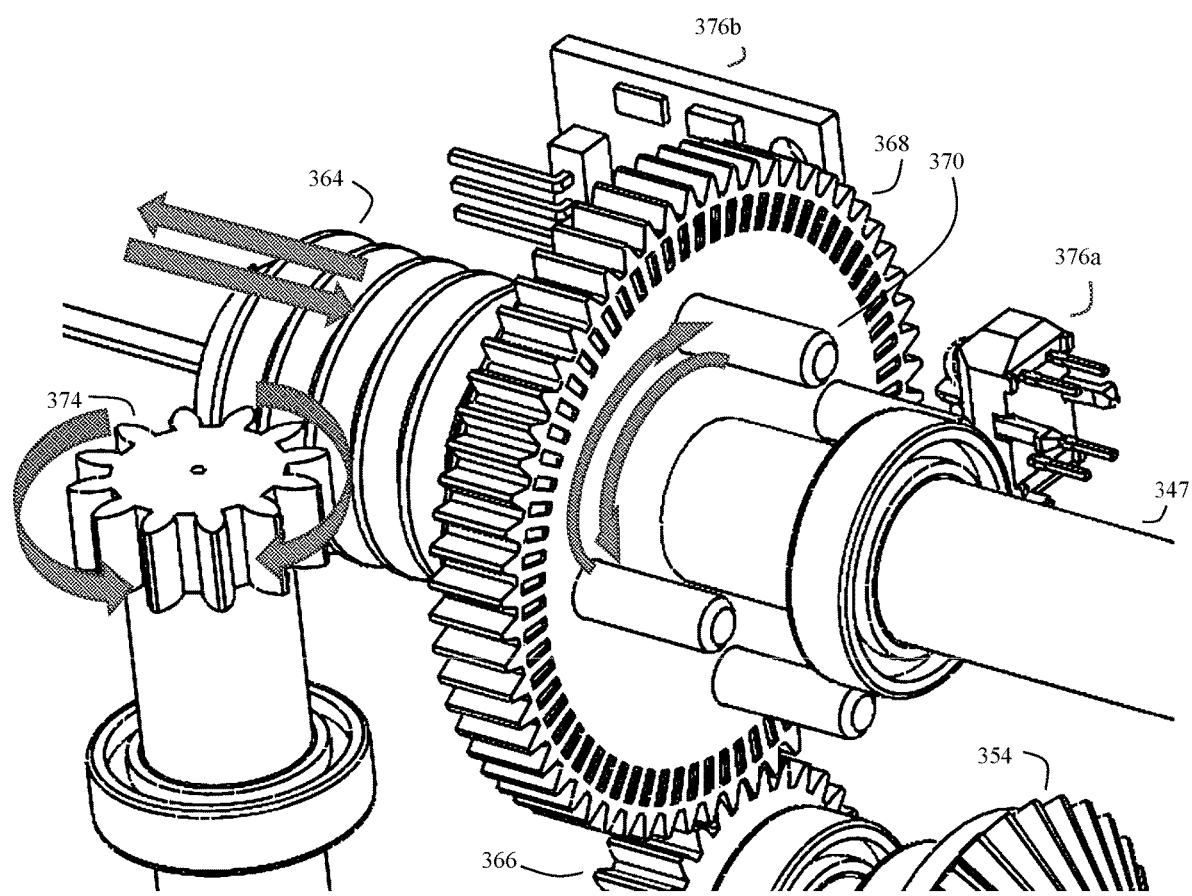
FIG. 25 shows a close-up view of the drive rack, transfer gear, and rotary gear system, as well as an example of how various sensors may be used to control and monitor the position of the drive.

FIG. 25 shows an alternative view showing a non-cross-sectional view of this portion of the system. Optional sensors (376*a*) and sensor electronics (376*b*) are also shown.

FIG. 25 shows a close-up view of the drive rack, transfer gear, and rotary gear system, as well as an example of how various sensors (376*a*, 376*b*) may be used to control and monitor the position of the drive.

Figure 26:
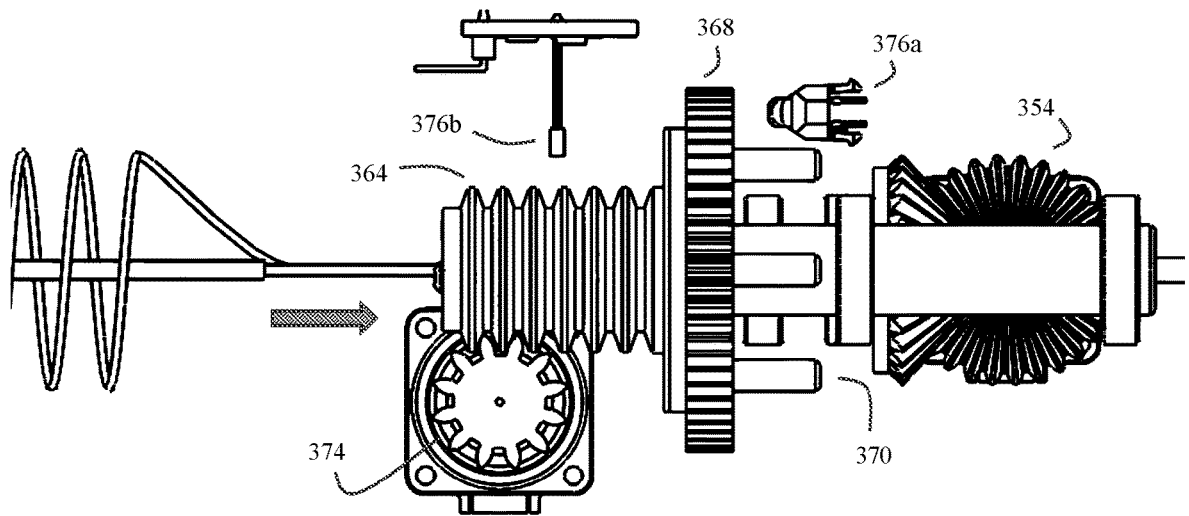
FIG. 26 shows one extreme position of the device's linear circular gear rack.
Figure 27:
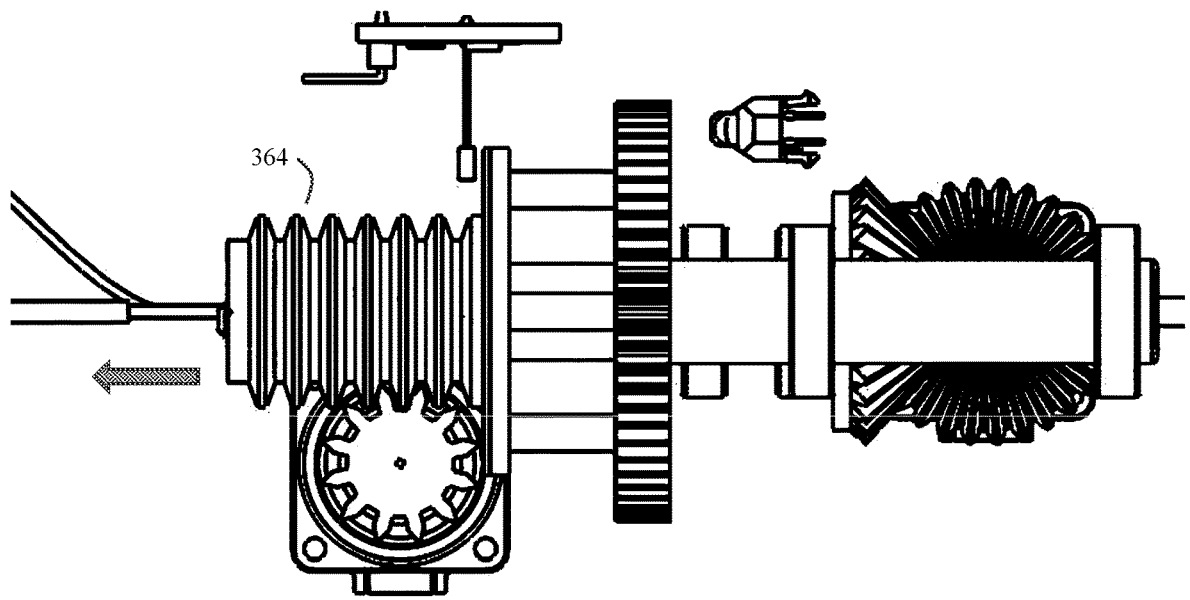
FIG. 27 shows a different extreme position of the device's linear circular gear rack.

FIG. 26 and FIG. 27 show how the rotary position for the Rotary Drive Gear may be tracked with sensors such as optical emitter/detector pairs and edge markings on the face of the gear. The closed loop linear position of the Linear Circular Gear Rack may be sensed by hall-effect sensors or other optical emitter/detector pairs in conjunction with a magnetic or reflective surface. Different types of sensors may also be used.

FIG. 26 and FIG. 27 show the extreme positions of the Linear Circular Gear Rack (364) for a single stage (e.g. 342). It is important to understand this rotary-linear drive in a simplified one-stage/one-catheter situation where the linear actuation rotates directly or 1:1 with the rotary stage. This rotation can go beyond 360 degrees in either direction without limitation and without the linear actuation mechanism causing the pull cables to become twisted. This is an important point because a key objective of the invention is to prevent cable twisting, which can interfere with the function of the catheter device.

FIG. 26 shows the relaxed position where there is no cable tension. FIG. 27 shows the full flexed state where the cable is fully tensioned by the Linear Pinion Gear (374) engaging and driving the Linear Circular Gear Rack (364) with the output flexing the catheter. This can then return to the relaxed state shown in FIG. 26.

FIG. 26 shows one extreme position of the device's linear, circular gear rack (374) (for a single stage such as any of 342). Here, the linear, circular pinion gear (374) has rotated clockwise and, by engaging with a ridge or ridges formed in the drive rack (364), has pushed the drive rack (364) and pins 370 to one furthest extent up against the rotary drive gear (368), thus releasing tension on one of the distal or proximal stage steering cables.

FIG. 27 shows a different extreme position of the device's linear, circular gear rack (for the same stage as above). Here the linear, circular pinion gear (374) has rotated counter-clockwise and, again by engaging with a ridge or ridges formed in the drive rack (364), has pulled the drive rack (364) and pins 370 to the other furthest extent thus creating tension on one of the distal or proximal stage steering cables. Here, the system's one or more sensors (376*a*, 376*b*) and processors (410) can again be used to adjust this tension to a desired extent.

Figure 28A:
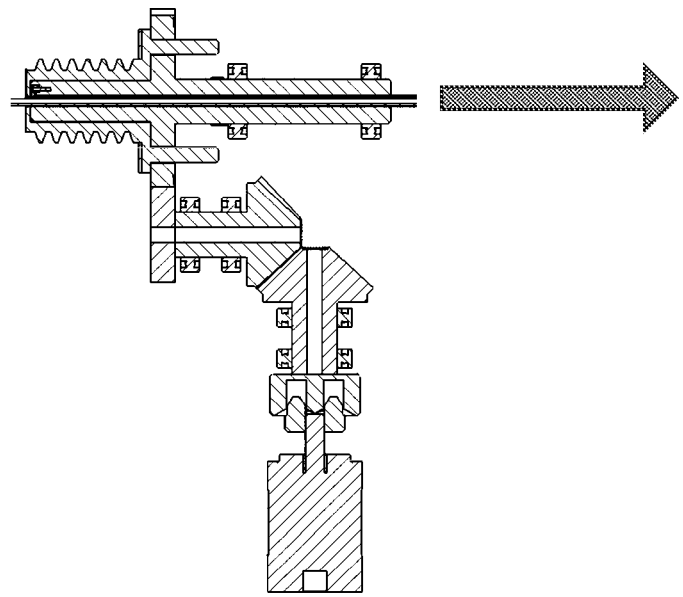
FIG. 28A shows a cross-sectional view of the rotary and linear drive system.
Figure 28B:
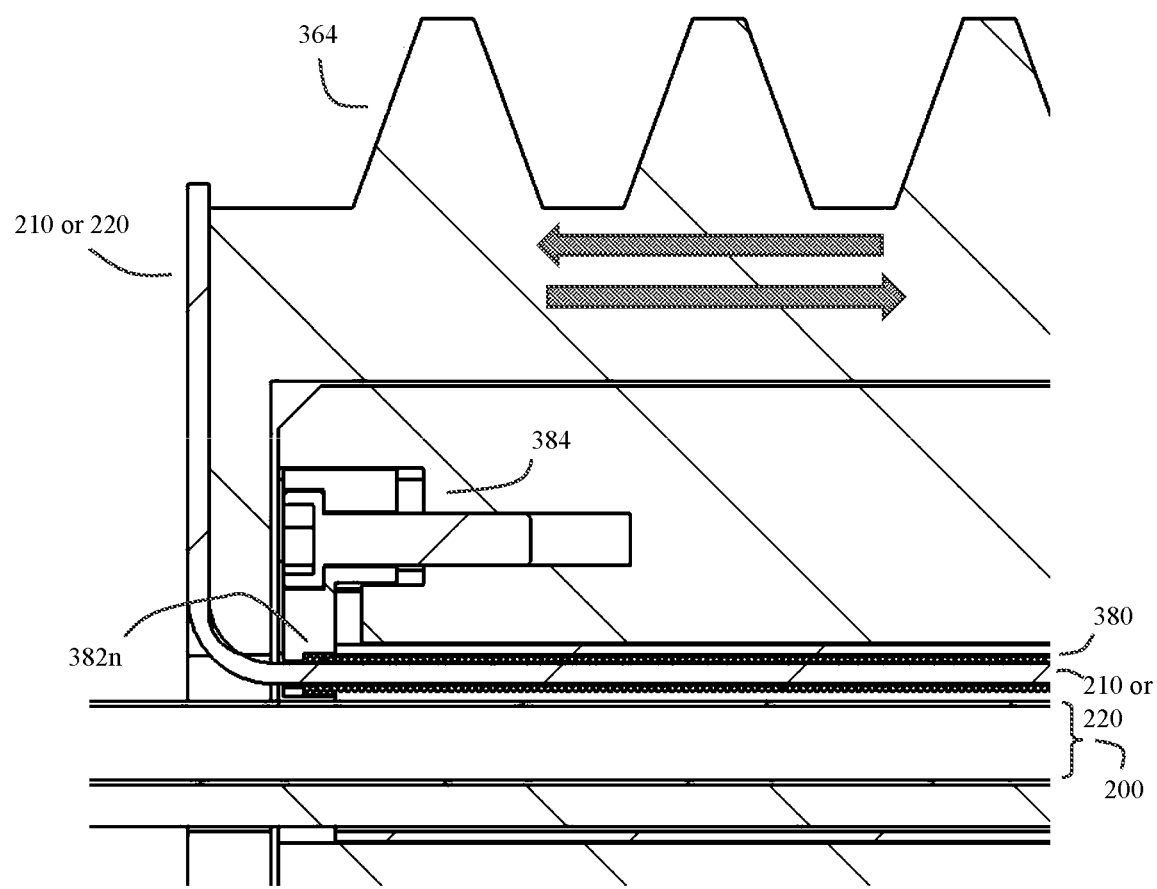
FIG. 28B shows further details of the drive rack previously shown in FIG. 29A.

FIG. 28A shows a cross-section of the rotary and linear drive system. FIG. 28B expands on a portion of FIG. 28A, and shows the position of the drive rack (364) and how the steering cable (220) is positioned as a result of movement of the linear circular pinion gear (374). This figure also shows an optional tightly wound isolation coil (380) that in some embodiments may surround (and shields) a significant portion of its respective steering cable (such as 220). This optional isolation coil (380) is often configured so that it has some extra length between the two optional isolation coil stops, such as (382*n*) and (386*d*). This means that the isolation coil has an uncompressed length that is a bit greater than the neutral axis of the catheter that it resides inside of. This optional isolation coil helps isolate the steering cable (220) tension such that the steering cable (flex cable) does not create tension force along the entire length of the catheter. Instead, due to the shielding or force-isolation property of the isolation coil (380), the tension force in the steering cable (220) is directed to only the flexible distal section of the catheter that this steering cable is designed to flex or curve.

Note that if no isolation coil is used, the isolation coil stops may also be omitted.

The underlying idea of the optional isolation coil is similar to the principle used on cable-operated hand brakes on bicycles and motorcycles. Mechanically, each isolation coil works by applying an equal but opposite force to its internal steering cable (220). As a result, until the steering cable force reaches its destination at the far distal end isolation stop (386*d*) where the steering cable (220) then protrudes beyond the isolation stop, the cable force is isolated. The steering cable force ends up being directed on the section catheter after the isolation coil ends (after 386*d*). This causes the catheter to flex from the point of where the cable is attached (e.g., tooling plate 220*t*, transition housing, or near far distal edge of catheter tubing) to the isolation coil end (386*d*).

Note that in FIG. 28A and FIG. 28B, the Linear Circular Gear Rack is not actuated, and the end of the catheter system controlled by that particular steering cable is in a relaxed state (large gray arrow straight).

FIG. 28A shows a cross-sectional view of the rotary and linear drive system. Here the drive system is in a first, "relaxed" state, similar to that shown in FIG. 26. In this configuration, there is lower tension on the distal (or proximal) steering cable, such as (220), and as a result, the relevant distal (108) portion of the catheter tends to be straight (not flexed).

Put alternatively, in some embodiments, each optional isolation coil (380) has an isolation coil compression. At least the near-isolation-coil end (382*n*) of the isolation coil is attached proximate to its respective flexing actuator in a manner that further enables this isolation coil compression to be adjusted. The device is further configured to adjust this isolation coil compression by a manual isolation coil compression adjuster and/or a compression actuator.

FIG. 28B shows further details of the drive rack (364) previously shown in FIG. 28A. Note that depending on which drive section (distal 342) is involved, then often the proximal portion of the distal steering cable (220) is affixed to the end of the dive rack. As previously discussed, to help prevent mechanical cross-talk between the steering cables and other parts of the apparatus, some or all steering cables (such as 220) may optionally pass through or traverse their own isolation coil (380). This isolation coil is hollow, and the interior of the coil has sufficient diameter so that the steering cable (220) can pass through this hollow interior freely. At the same time, the isolation coil helps to shield or "isolate" the movement of the steering cable (220) from the rest of the catheter device, at least while the steering cable (220) is inside the isolation coil.

As previously shown, this isolation coil, if present, generally runs the entire length of the catheter up the distal coil stop (107*b*). This distal coil stop (107*b*) is usually positioned at the isolation transition coupler (107*a*). From that point, the steering cable (220) then runs the usually shorter distance up the distal catheter portion (108) to its destination (usually at or near the distal tool plate 109, such as 220*t*, depending on the type of steering cable).

The optional isolation coil has a near end (382*n*) and a far end (see FIG. 5A, 7A, 10A, 386*d*). The near (e.g., proximal) portion of the steering cable is attached (for example, clamped) to the flexing actuator (here the end of 364). The near end of the isolation cable (382*n*) is also attached in a manner that allows the steering cable to movably protrude past the near isolation coil end (382*n*), while blocking the axial movement of the isolation coil at this end. This isolation coil attachment can be done by various methods, such as by an adjustable isolation coil stop screw (384) which can also be used for setting the isolation coil compression. This compression setting can be a very fine adjustment for an isolation coil is tightly wound.

Put alternatively, in some embodiments, at least one distal stage steering cable (220) may be further disposed inside an isolation coil (380) comprising a far-isolation-coil-end (386*d*) and a near-isolation-coil-end (382*n*). Here, the far-isolation-coil-end is attached proximate to a distal terminus of its corresponding steering cable in a manner (such as distal coil stop 107*b*) that allows its corresponding steering cable (220) to movably protrude past the far-isolation-coil-end (386*d*) while blocking axial movement of the far-isolation-coil-end.

Further, each near-isolation-coil-end (382*n*) may be attached proximate to its respective flexing actuator in a manner that allows its corresponding steering cable (220) to movably protrude past the near-isolation coil end while blocking the axial movement of the near-isolation-coil-end. In a preferred embodiment, the device is further configured to rotate the at least one isolation coil in a 1:1 ratio with any rotation of its respective steering cable and its respective distal stage. This scheme thus helps or enables the variable tension applied by each respective flexing actuator to be isolated to its respective steering cable while the cable is inside its respective isolation coil.

Note further that, as previously discussed, each isolation coil (380) has an isolation coil compression. Further, the near-isolation-coil end (382*n*) is attached proximate to its respective flexing actuator in a manner that further enables this isolation coil compression to be adjusted. The device may also be further configured to adjust this isolation coil compression by any of a manual isolation coil compression adjuster and/or a compression actuator.

In FIG. 28B, a detail of the distal drive section (342) is shown, and a portion of the hollow torque shaft (200) is also shown. In some embodiments, according to the invention, at least one torque shaft actuator, such as (350*r*1) may be used to apply torque to the hollow torque shaft (200).

Figure 29A:
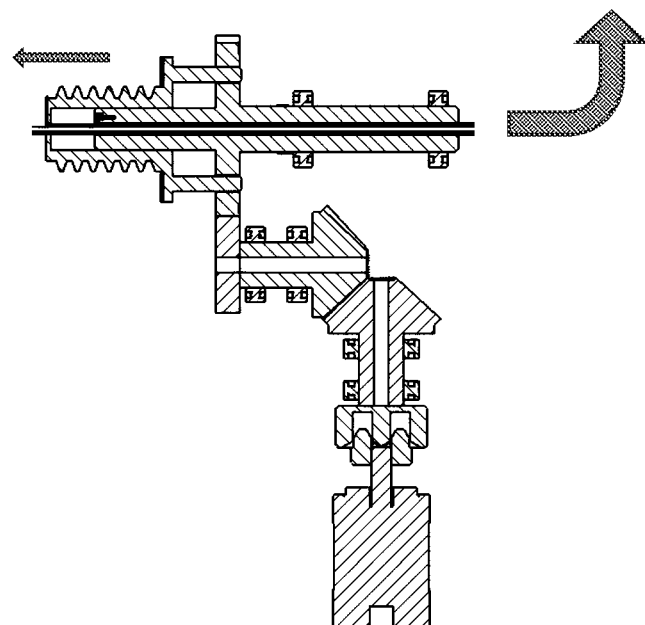
FIG. 29A shows a cross-sectional view of the rotary and linear drive system.
Figure 29B:
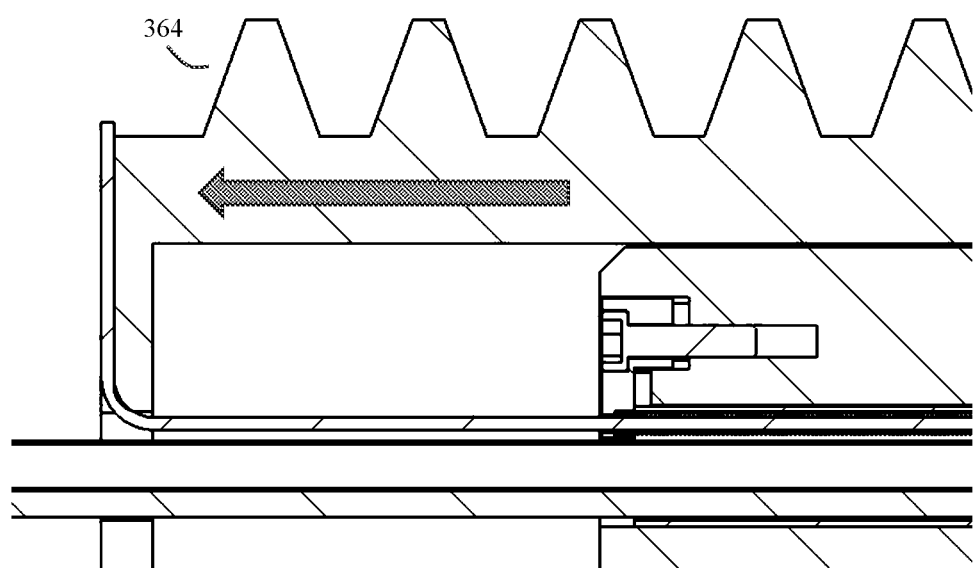
FIG. 29B shows further details of FIG. 30A.

By contrast, in FIG. 29A and FIG. 29B, the Linear Circular Gear Rack is actuated, and the catheter system is in the flexed state (large gray arrow turned up)

FIG. 29A shows a cross-sectional view of the rotary and linear drive system. Here the drive is in a second "actuated or flexed" state. Here the relative motion of the flexing actuator (364) has moved the distal or proximal steering cable (220) towards full tension. As a result, this steering cable tugs on its respective other end of the catheter, causing either the outer distal (108) catheter tube to become fully flexed or curved.

FIG. 29B shows further details of FIG. 29A. In the relaxed state shown in FIG. 28A/28B or flexed state shown in FIG. 29A/29B, the distal drive section (342) can be rotating along with the respective distal or proximal catheters at any rotational position.

Figure 30:
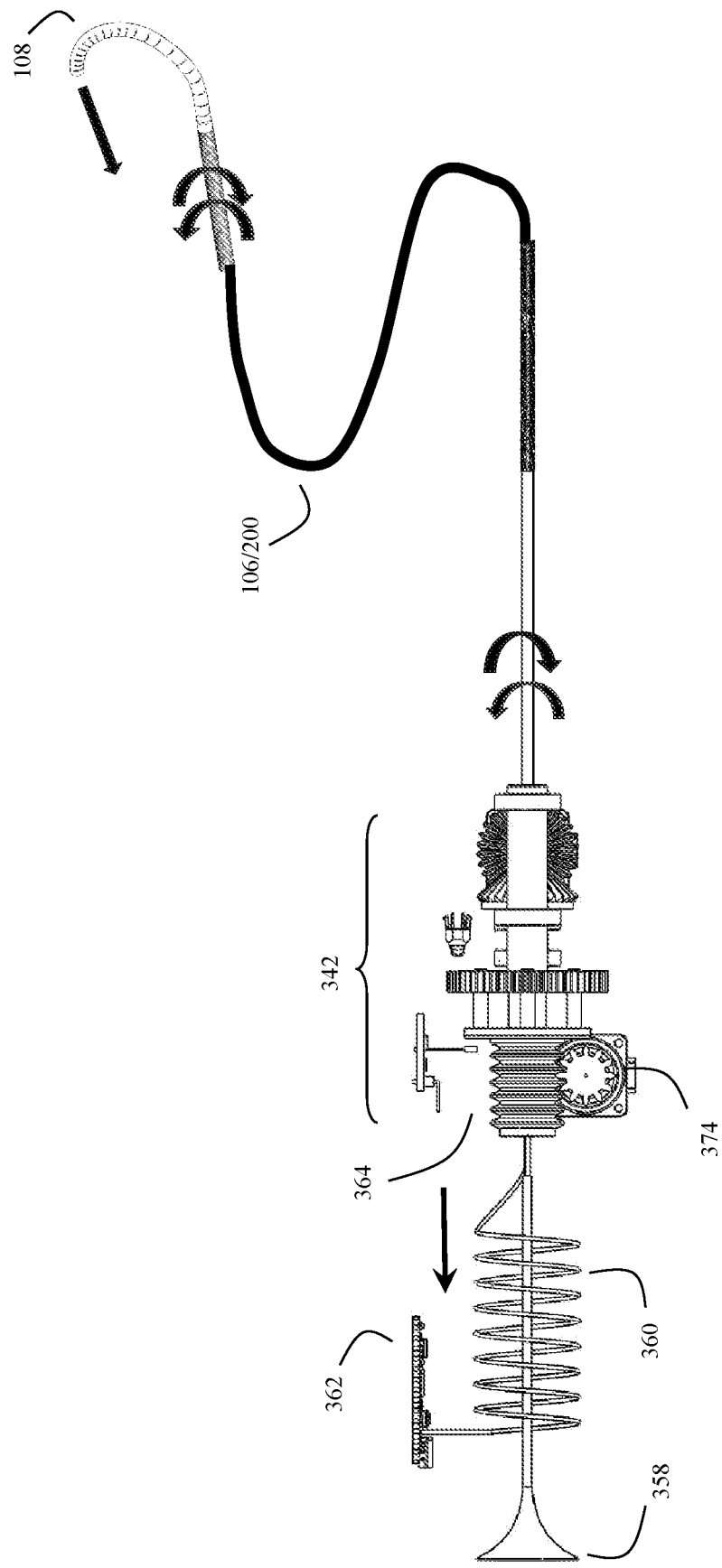
FIG. 30 shows an overview of the complete system, including both the drive system and the catheter.

FIG. 30 shows an overview of the system.

FIG. 30 (right side) shows an overview of how the rotary and linear drive systems can drive the catheter. As previously discussed, Here, the distal stage (108) is flexed and rotating either clockwise or counterclockwise, depending on its actuator. The distal flexion can be by tension transmitted by the distal stage steering cable (220) to the distal tool plate (109). The distal stage rotation can be transmitted by the torque shaft (200). At the same time, the proximal stage (106) is also flexed and rotating either clockwise or counterclockwise as per the distal stage because the two stages are connected by the isolation transition coupler (107*a*).

FIG. 30 left side shows a close-up of a portion of the rotary and linear drive system (here 342) during the driving process of the multi-stage catheter shown on the right side of FIG. 30.

In this figure, the Circular Linear Gear Rack (drive rack 364) has been extended by the driving force of the Linear Circular Pinion Gear (374). This controls the tension in the distal steering cable (220), causing the outer distal (108) portions of the catheter to bend.

Disposable or Reposable Housing Embodiments

Figure 31B:
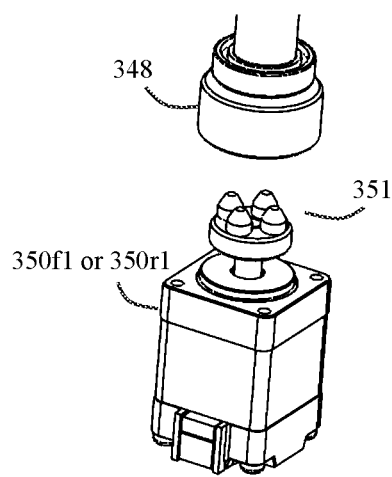
FIG. 31B shows a detail of how a motor coupler from a gear train from the disposable housing/cartridge may interact with the drive pins of an actuator.
Figure 31C:
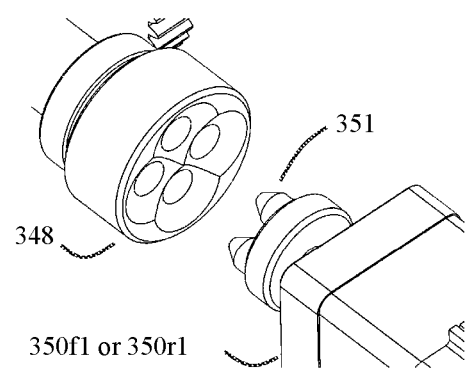
FIG. 31C shows another view of how a coupler from a gear train from the disposable housing/cartridge may interact with the drive pins of an actuator.

FIGS. 31A, 31B, and 31C show how the proximal drive side of the catheter can be contained in a disposable or reposable housing. The disposable housing can be coupled to an array of drive motors that are attached to a fixed platform such as the robotic arm shown in FIG. 32. The motors have a drive hub with protruding pins attached to the output shaft. The motor hubs drive pins engage with a coupler that is directly connected to the drive train gears of the cartridge.

FIG. 31A shows how a disposable/reposable housing (388) may contain the drive side (or gear train) of the catheter driving assembly. This in turn may interact with the various actuators (e.g. electric motors) disposed on a robotic arm or other platform.

FIG. 31B shows a detail of how a motor coupler (348) from a gear train from the disposable housing (388) may interact with the drive pins (351) of an actuator (such as 350*f*1, or 350*r*1).

FIG. 31C shows another view of how a coupler (348) from a gear train from the disposable housing (388) may interact with the drive pins (351) of an actuator (such as 350*f*1 or 350*r*1).

In some embodiments, the at least one contacting mechanism may comprise at least one gear assembly (for example, any of 354, 364, 366, 368, 370, 374 or other gears that conduct force from one or more actuators to various parts of the catheter). Here, at least portions of this gear assembly may be configured in a disposable or reposable cartridge (388) that can be reversibly coupled and decoupled from the various one processor-controlled electromagnetic actuators (such as any of 350*f*1, 350*f*2, 350*r*1, 350*r*2). Thus, the electromagnetic actuators may be more permanently mounted on a robotic arm, while the disposable and preferably sterilized gears in the cartridge (388) can be mounted and either discarded or refurbished for subsequent use.

Note that in some embodiments, the contacting mechanism may alternatively comprise a lever/finger or fork with a fulcrum connected to an actuator that rests inside of a groove or over a protruding ring of the rotatable slidable element. This lever/finger or fork can push or pull against either edge in the groove or over the ring with two edges.

Further Methods of Actuating a Rotary Robotic Catheter

To generalize the concepts above, other actuation methods that do not use gears are may also be used.

The rotary or linear actuation can be driven by electromagnetic, shape memory alloy actuators, airpower actuators, vacuum actuators, fluid actuators, etc.

In some alternative embodiments, An electromagnetic linear actuator (motor) may be used that rotates about the rotary drive motor axis. This embodiment does not need to use drive pins to keep the linear actuators synchronized with the rotary actuators. Instead, a rigid mount can be used to fix the linear actuator to the rotary actuator. These motors can be open-loop or closed-loop DC or AC-type motors. The electrical wires for the spinning motors are managed by providing extra length such that the motors can rotate beyond 360 degrees in either direction depending on the wire coil loop size.

In another alternative embodiment where the Distal and Proximal stages are coupled stages that are driven by alternative electromagnetic actuator systems. Here the rotational actuation is powered by through-shaft motors, and the linear actuation is powered by linear electro-magnetic motors that pull the flex cables. In this embodiment, electrical motor wire management is unnecessary since both the rotary and linear motors can be of a through-hole type design.

Rotary-Linear Robotic Cather System with Independently Rotatable, Flexing, and Slidable Catheters In some embodiments, the system may use one or more linear actuator motors employing a pulley spinning about a through-hole motor.

Figure 32:
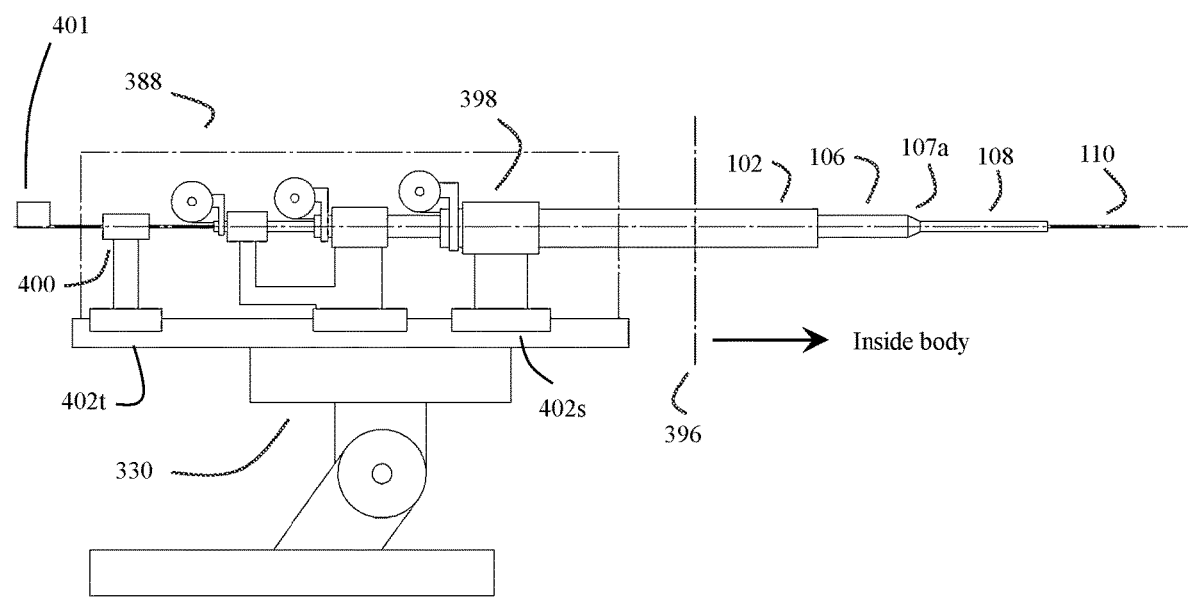
FIG. 32 shows an alternate view of the rotary-linear robotic catheter.

FIG. 32 shows an alternate view of the rotary-linear robotic catheter system with independently rotatable, flexing, and slidable catheters. Note that while operating on a patient, often at least the distal portion of the sheath (102), and the remaining distal components (e.g. 106, 107*a*, 108, 110, etc.) be inserted into the patient (e.g., catheter components to the right of the dividing line 396). By contrast, the various actuators, gears, robotic arms, and other portions of the system to the left of diving line 396 will remain outside of the patient. These later systems may be mounted on a robotic arm, such as previously described (330).

Note that in some embodiments, a similar type 1:1 synchronized linear and rotary drive system, and optional sheath steering cable(s) may also be used to control the movement of the sheath (102) while inside the body. This optional sheath system is shown as (398). Additionally, other actuator systems, such as therapy payload conduit dispensing system (400) may also be used. Here the therapy delivery or producing unit itself is shown as (401).

FIG. 32 also shows that in some embodiments, the device may further comprise at least one payload dispensing actuator (402*t*) configured to move at least one payload along the working channel by advancing or retracting a payload dispensing conduit along this working channel (228).

FIG. 32 also shows that in some embodiments, according to the invention, at least the proximal portions of the proximal stage hollow catheter (106) may be disposed within at least one hollow sheath (102). This at least one hollow sheath may be configured to enable at least portions of the multi-stage catheter device to (axially) protrude or retreat inside and outside of this at least one hollow sheath, depending on forces applied to the at least one hollow sheath (102) and at least the proximal stage hollow catheter (106). Here, the axial movement of this hollow sheath may be controlled according to a sheath translation stage actuator (402s) and optionally by processor (410) or another controller.

Put alternatively, FIG. 32 also shows that in some embodiments, the device may be further configured with at least proximal portions of the proximal stage hollow catheter (106) disposed within at least one hollow sheath (102). Here, the at least one hollow sheath may be configured to enable at least portions of the multi-stage catheter device to protrude or retreat inside and outside the sheath, depending on forces applied to the sheath and/or the proximal stage hollow catheter. Further, the device may be configured with a sheath translation stage actuator (402s) configured to control the sheath's axial movement.

Tracking the System of Catheters

For the Rotary-Linear Robotic Cather System with Independently Rotatable, Flexing, and Slidable Catheters, it will often be useful to provide a method of tracking catheter location in real-time while the catheter is in the patient.

In some embodiments, each catheter stage may include a radio-opaque component, such as a platinum ring. When used with an imaging system, such as Real-time CT, these radio-opaque elements enable the position of each catheter tip to be tracked. Thus, each far distal catheter axis is defined by two points at any time. This allows the position of the far distal ring of the catheter section and the next proximal ring to be determined.

The invention claimed is:

1. A catheter device for traversing internal body passages, said catheter device comprising:
    a hollow catheter comprising at least one stage, said hollow catheter comprising a distal portion and a proximal portion;
    said proximal portion comprising a hollow torque shaft configured to receive torque from a rotary shaft actuator;
    said hollow catheter configured so that torque applied to said hollow torque shaft is conveyed to said distal portion;
    said device further comprising conduits comprising at least one tensioning cable extending along said catheter from said proximal portion to said distal portion, each said tensioning cable comprising a steering cable;
    said hollow torque shaft and said distal portion further comprising a working channel configured to convey at least one other conduit through said proximal portion and said distal portion to at least a distal tool plate mounted on a distal end of said distal portion;
    wherein said at least one said tensioning cables comprise at least one distal portion steering cable that is configured to convey distal portion steering force to said distal tool plate, causing said distal tool plate and said distal portion to move according to said distal portion steering force;
    wherein said device further comprises:
    at least one distal portion tensioning actuator configured to flex and unflex said end of said distal portion by creating and releasing tension on at least one of said at least one distal portion steering cables;
    said at least one distal portion tensioning actuator further configured to rotate said at least one distal portion steering cable in a 1:1 ratio with any rotation of at least said distal portion caused by torque from said rotary shaft actuator.

2. The device of claim 1, wherein any of said distal portion and proximal portion are surrounded on their exterior surfaces by a flexible polymeric jacket which may be either continuous or discontinuous between sections.

3. The device of claim 1, further comprising at least one elastic element configured along at least a portion of said catheter to oppose forces applied by at least one of said at least one tensioning cables.

4. The device of claim 1, wherein said distal tool plate is configured with an opening with a distal tool plate opening diameter that is less than or equal to an inner diameter of said distal portion.

5. The device of claim 1, wherein at least some of said conduits comprise electrical conduits configured to transmit any of electrical power or electrical signals to any of probes, sensors, or other electrically activated devices disposed on or passing through said distal tool plate.

6. The device of claim 1, wherein said at least some of said conduits comprise any of optical fibers or hollow tubes configured to convey any of optical, electromagnetic, or radiofrequency (RF) signals or chemicals to or from devices disposed on said distal tool plate.

7. The device of claim 1, wherein said hollow catheter is a multi-stage catheter wherein said distal portion is a distal stage hollow catheter and said proximal portion is a different proximal stage hollow catheter;
    one end of said distal stage hollow catheter affixed to an end of said hollow torque shaft by a junction between one end of said distal stage hollow catheter and said hollow torque shaft so that torque applied to said hollow torque shaft is conveyed to said distal stage hollow catheter.

8. The device of claim 1, wherein any of said distal portion and said proximal portion comprise any of a woven, non-woven, or continuous material or other material with plurality of slits or openings, along at least a portion of their circumference;
    said material having positions and dimensions configured to facilitate traversal of said device through a series of branching body lumens of progressively smaller internal diameters.

9. The device of claim 1, wherein at least proximal portions of said proximal portion are disposed within at least one hollow sheath, at least one of said at least one hollow sheath configured to enable at least portions of said catheter device to protrude or retreat inside and outside of said at least one hollow sheath, depending on forces applied to said at least one hollow sheath and at least said proximal portion.

10. The device of claim 1, wherein at least portions of said at least one distal portion steering cable are further disposed inside an isolation coil comprising a far-isolation-coil-end and a near-isolation-coil-end;
    each said far-isolation-coil-end is attached proximate to a distal terminus of its corresponding steering cable in a manner that allows said corresponding steering cable to movably protrude past said far-isolation-coil-end while blocking axial movement of said far-isolation-coil-end;
    each said near-isolation-coil-end is attached proximate to its respective flexing actuator in a manner that allows said corresponding steering cable to movably protrude past said near-isolation coil end while blocking axial movement of said near-isolation-coil-end.

11. The device of claim 1, wherein said at least one distal portion tensioning actuator comprises at least one contacting mechanism, at least one electromagnetic actuator, and at least one processor configured to control said at least one electromagnetic actuator;

wherein said device further comprises at least one motion or position sensor; and wherein said at least one processor is further configured to use input from said at least one motion or position sensor to control said at least one electromagnetic actuator.

12. The device of claim 1, any of said rotary shaft actuator and said distal portion tensioning actuators comprise electromagnetic actuators; and wherein said rotary shaft actuator drives said hollow catheter to rotate about an axis of said catheter.

13. A multi-stage catheter device for traversing internal body passages, said multi-stage catheter device comprising:

a distal stage hollow catheter and a different proximal stage hollow catheter;

said different proximal stage hollow catheter comprising a hollow torque shaft configured to receive torque from a rotary shaft actuator;

one end of said distal stage hollow catheter affixed to an end of said hollow torque shaft by a junction between one end of said distal stage hollow catheter and said hollow torque shaft so that torque applied to said hollow torque shaft is conveyed to said distal stage hollow catheter;

said device further comprising conduits comprising at least one tensioning cable extending along said catheter from said proximal stage to said distal stage, each said tensioning cable comprising a steering cable;

said hollow torque shaft and said distal stage hollow catheter further comprising a working channel configured to convey at least one other conduit through said proximal stage hollow catheter and said distal stage hollow catheter to at least a distal tool plate mounted on a distal end of said distal stage hollow catheter;

wherein said at least one said tensioning cables comprise at least one distal stage steering cable that is configured to convey distal stage steering force to said distal tool plate, causing said distal tool plate and said distal stage catheter to move according to said distal stage steering force;

said device further comprising:

at least one distal stage tensioning actuator configured to flex and unflex said end of said distal stage hollow catheter by creating and releasing tension on at least one of said at least one distal stage steering cables;

said at least one distal stage tensioning actuator further configured with said rotary shaft actuator to rotate said at least one distal stage steering cable in a 1:1 ratio with any rotation of at least said distal stage hollow catheter caused by torque from said rotary shaft actuator.

14. The device of claim 13, wherein said at least one distal stage tensioning actuator comprises at least one contacting mechanism, at least one electromagnetic actuator, and at least one processor configured to control said at least one electromagnetic actuator;

wherein said device further comprises at least one motion or position sensor; and wherein said at least one processor is further configured to use input from said at least one motion or position sensor to control said at least one electromagnetic actuator.

15. The device of claim 14, wherein said at least one contacting mechanism comprises at least one gear assembly; and wherein at least portions of said gear assembly are configured in a disposable or reposable cartridge that can be reversibly coupled and decoupled from said at least one electromagnetic actuator.

16. The device of claim 13, further comprising:

at least one payload dispensing actuator configured to move at least one payload along said working channel by advancing or retracting a payload dispensing conduit along said working channel.

17. The device of claim 13, wherein any of said at least one distal stage steering cable is further disposed inside an isolation coil comprising a far-isolation-coil-end and a near-isolation-coil-end;

each said far-isolation-coil-end is attached proximate to a distal terminus of its corresponding steering cable in a manner that allows said corresponding steering cable to movably protrude past said far-isolation-coil-end while blocking axial movement of said far-isolation-coil-end;

each said near-isolation-coil-end is attached proximate to its respective flexing actuator in a manner that allows said corresponding steering cable to movably protrude past said near-isolation coil end while blocking axial movement of said near-isolation-coil-end;

said device further configured to rotate each said isolation coil in a 1:1 ratio with any rotation of its respective steering cable and its respective distal stage caused by torque from said rotary shaft actuator;

thus enabling variable tension applied by each said respective flexing actuator to be isolated to its respective steering cable while said cable is inside its respective isolation coil.

18. The device of claim 17, wherein each said isolation coil has an isolation coil compression;

at least said near-isolation-coil end is attached proximate to its respective flexing actuator in a manner that further enables said isolation coil compression to be adjusted;

said device further configured to adjust said isolation coil compression by any of a manual isolation coil compression adjuster and a compression actuator.

19. The device of claim 13, wherein any of said distal stage and proximal stage are surrounded on their exterior surfaces by a flexible polymeric jacket which may be either continuous or discontinuous between sections.

20. The device of claim 13, further comprising at least one elastic element configured along at least a portion of said catheter to oppose forces applied by at least one of said at least one tensioning cables.

21. The device of claim 13, wherein said device is further configured with at least proximal portions of said proximal stage hollow catheter disposed within at least one hollow sheath;

at least one of said at least one hollow sheath configured to enable at least portions of said multi-stage catheter device to protrude or retreat inside and outside of said at least one hollow sheath, depending on forces applied to said at least one hollow sheath and at least said proximal stage hollow catheter;

wherein said device is further configured with a sheath translation stage actuator configured to further control axial movement of said hollow sheath.

\* \* \* \* \*